US012690804B2

(12) United States Patent
Akagawa

(10) Patent No.: US 12,690,804 B2
(45) Date of Patent: Jul. 28, 2026

(54) BIOANALYSIS SYSTEM FOR IDENTIFICATION OF PORE DIAMETER AND PORE TYPE

(71) Applicant: NEC Corporation, Tokyo (JP)

(72) Inventor: Takeshi Akagawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 394 days.

(21) Appl. No.: 18/276,189

(22) PCT Filed: Feb. 18, 2021

(86) PCT No.: PCT/JP2021/006123
§ 371 (c)(1),
(2) Date: Aug. 7, 2023

(87) PCT Pub. No.: WO2022/176106
PCT Pub. Date: Aug. 25, 2022

(65) Prior Publication Data
US 2024/0298959 A1      Sep. 12, 2024

(51) Int. Cl.
*A61B 5/00* (2006.01)
*A61B 5/107* (2006.01)
(Continued)

(52) U.S. Cl.
CPC ............ *A61B 5/441* (2013.01); *A61B 5/0073* (2013.01); *A61B 5/1079* (2013.01); *G06T 7/0016* (2013.01); *G06T 7/62* (2017.01); *G06T 12/30* (2026.01); *G06V 10/62* (2022.01); *G06V 20/64* (2022.01); *G16H 50/30* (2018.01); *A61B 2576/02* (2013.01);
(Continued)

(58) Field of Classification Search
None
See application file for complete search history.

(56) References Cited

U.S. PATENT DOCUMENTS

| | | |
|---|---|---|
| 2006/0129214 A1 | 6/2006 | Da Silva et al. |
| 2006/0142750 A1 | 6/2006 | Da Silva et al. |

(Continued)

FOREIGN PATENT DOCUMENTS

| | | | | |
|---|---|---|---|---|
| CN | 112274110 A | * | 1/2021 | .......... G06T 7/0012 |
| JP | 2003-210416 A | | 7/2003 | |

(Continued)

OTHER PUBLICATIONS

International Search Report for PCT Application No. PCT/JP2021/006123, mailed on Apr. 20, 2021.

*Primary Examiner* — Andrew M Moyer
*Assistant Examiner* — Caroline E. Depalma

(57) ABSTRACT

A bioanalysis system includes: an acquisition unit that obtains a plurality of two-dimensional data with different depths in a skin of a living body; a position identification unit that identifies a position of a pore part in the skin of the living body from at least one of the plurality of two-dimensional data; an extraction unit that extracts a diameter of the pore part from each of the plurality of two-dimensional data; and a type identification unit that identifies a type of the pore part, on the basis of the diameter of the pore part. According to such a bioanalysis system, it is possible to properly identify the position and the type of the pore part in the skin of the living body.

8 Claims, 32 Drawing Sheets

(51) Int. Cl.

| | |
|---|---|
| *G06T 7/00* | (2017.01) |
| *G06T 7/62* | (2017.01) |
| *G06T 12/30* | (2026.01) |
| *G06V 10/62* | (2022.01) |
| *G06V 20/64* | (2022.01) |
| *G16H 50/30* | (2018.01) |

(52) U.S. Cl.
CPC .............. *G06T 2207/10101* (2013.01); *G06T 2207/30088* (2013.01); *G06T 2207/30201* (2013.01); *G06T 2210/41* (2013.01); *G06T 2211/456* (2023.08)

(56) References Cited

U.S. PATENT DOCUMENTS

| | | | |
|---|---|---|---|
| 2017/0319065 A1* | 11/2017 | Kimura | A61B 5/0077 |
| 2019/0125247 A1 | 5/2019 | Saeki et al. | |
| 2019/0295728 A1* | 9/2019 | Jeong | G05B 15/02 |

FOREIGN PATENT DOCUMENTS

| | | | | |
|---|---|---|---|---|
| JP | 2004-337317 | A | | 12/2004 |
| JP | 2005-345297 | A | | 12/2005 |
| JP | 2007225349 | A | * | 9/2007 |
| JP | 2008-522756 | A | | 7/2008 |
| JP | 2010051347 | A | * | 3/2010 |
| JP | 2014-120005 | A | | 6/2014 |
| JP | 2016-054986 | A | | 4/2016 |
| JP | 6245590 | B1 | | 12/2017 |
| JP | 2020-500611 | A | | 1/2020 |
| KR | 10-2123101 | B1 | | 6/2020 |
| WO | 2019/170688 | A1 | | 9/2019 |

* cited by examiner

S11

S12

S13

S14

S11

S12

S13

S21

TWO-DIMENSIONAL
DATA OF DEPTH D1

TWO-DIMENSIONAL
DATA OF DEPTH D2

TWO-DIMENSIONAL
DATA OF DEPTH D3

TWO-DIMENSIONAL
DATA OF DEPTH D4

BIOANALYSIS SYSTEM FOR IDENTIFICATION OF PORE DIAMETER AND PORE TYPE

This application is a National Stage Entry of PCT/JP2021/006123 filed on Feb. 18, 2021, the contents of all of which are incorporated herein by reference, in their entirety.

TECHNICAL FIELD

This disclosure relates to technical fields of a bioanalysis system, a bioanalysis method, and a computer program that analyze a living body.

BACKGROUND ART

A known system of this type analyzes information about a skin of a living body. For example, Patent Literature 1 discloses that optical interferometry may be used when images around skin pores are captured. Patent Literature 2 discloses a technique/technology of performing an analyze of a thickness of an epidermis by using three-dimensional tomography images. Patent Literature 3 discloses a technique/technology of obtaining optical coherence tomography images of pores in the skin. Patent Literature 4 discloses a technique/technology of diagnosing a skin condition by processing optical interference signals. Patent Literature 5 discloses a technique/technology of photographing optical coherence tomography images of pores in the skin and measuring a distance in the images.

CITATION LIST

Patent Literature

Patent Literature 1: JP2004-337317A
Patent Literature 2: JP2007-225349A
Patent Literature 3: JP2016-054986A
Patent Literature 4: Japanese Patent No. 6245590
Patent Literature 5: JP2020-500611A

SUMMARY

Technical Problem

This disclosure aims to improve the related techniques/technologies described above.

Solution to Problem

A bioanalysis system according to an example aspect of this disclosure includes: an acquisition unit that obtains a plurality of two-dimensional data with different depths in a skin of a living body; a position identification unit that identifies a position of a pore part in the skin of the living body from at least one of the plurality of two-dimensional data; an extraction unit that extracts a diameter of the pore part from each of the plurality of two-dimensional data; and a type identification unit that identifies a type of the pore part, on the basis of the diameter of the pore part.

A bioanalysis method according to an example aspect of this disclosure includes: obtaining a plurality of two-dimensional data with different depths in a skin of a living body; identifying a position of a pore part in the skin of the living body from at least one of the plurality of two-dimensional data; extracting a diameter of the pore part from each of the plurality of two-dimensional data; and identifying a type of the pore part, on the basis of the diameter of the pore part.

A computer program according to an example aspect of this disclosure operates a computer to: obtain a plurality of two-dimensional data with different depths in a skin of a living body; identify a position of a pore part in the skin of the living body from at least one of the plurality of two-dimensional data; extract a diameter of the pore part from each of the plurality of two-dimensional data; and identify a type of the pore part, on the basis of the diameter of the pore part.

DESCRIPTION OF EXAMPLE EMBODIMENTS

Hereinafter, a bioanalysis system, a bioanalysis method, and a computer program according to example embodiment will be described with reference to the drawings.

First Example Embodiment

Figure 1:
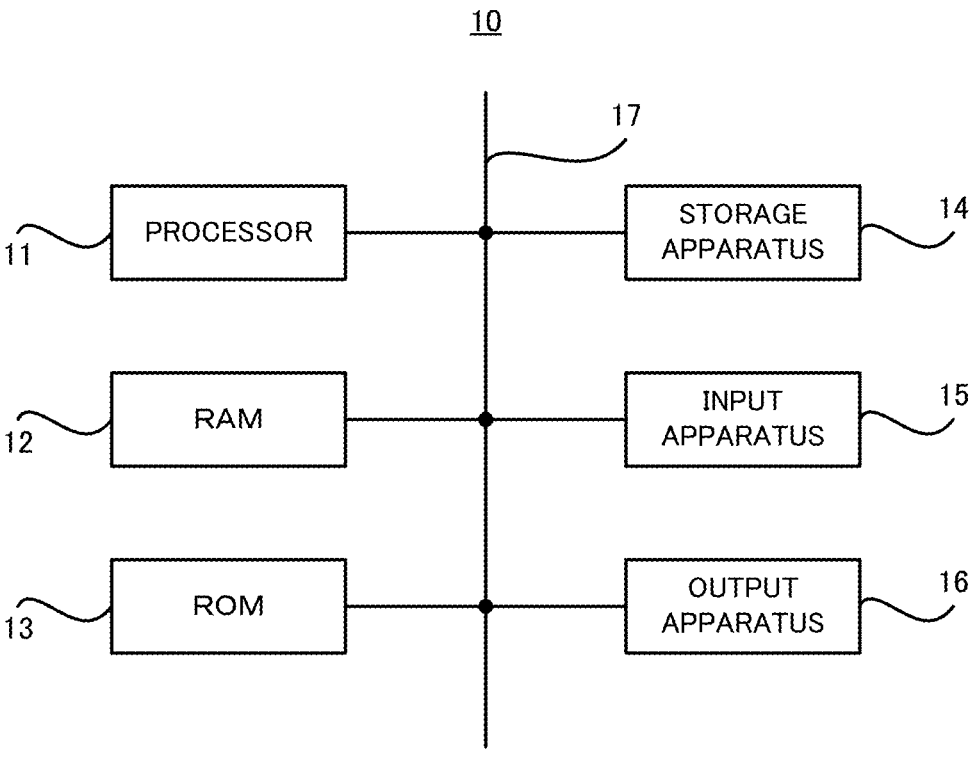
FIG. 1 is a block diagram illustrating a hardware configuration of a bioanalysis system according to the first example embodiment.

A bioanalysis system according to a first example embodiment will be described with reference to FIG. 1 to FIG. 3.
(Hardware Configuration)
First, with reference to FIG. 1, a hardware configuration of the bioanalysis system according to the first example embodiment will be described. FIG. 1 is a block diagram illustrating the hardware configuration of the bioanalysis system according to the first example embodiment.

As illustrated in FIG. 1, a bioanalysis system 10 according to the first example embodiment includes a processor 11, a RAM (Random Access Memory) 12, a ROM (Read Only Memory) 13, and a storage apparatus 14. The bioanalysis system 10 may further include an input apparatus 15 and an output apparatus 16. The processor 11, the RAM 12, the ROM 13, the storage apparatus 14, the input apparatus 15, and the output apparatus 16 are connected through a data bus 17.

The processor 11 reads a computer program. For example, the processor 11 is configured to read a computer program stored by at least one of the RAM 12, the ROM 13 and the storage apparatus 14. Alternatively, the processor 11 may read a computer program stored in a computer-readable recording medium by using a not-illustrated recording medium reading apparatus. The processor 11 may obtain (i.e., read) a computer program from a not-illustrated apparatus disposed outside the bioanalysis system 10, through a network interface. The processor 11 controls the RAM 12, the storage apparatus 14, the input apparatus 15, and the output apparatus 16 by executing the read computer program. Especially in this example embodiment, when the processor 11 executes the read computer program, a functional block for analyzing the skin of a living body is realized or implemented in the processor 11. An example of the processor 11 includes a CPU (Central Processing Unit), a GPU (Graphics Processing Unit), a FPGA (field-programmable gate array), a DSP (Demand-Side Platform), and an ASIC (Application Specific Integrated Circuit). The processor 11 may use one of the examples described above, or may use a plurality of them in parallel.

The RAM 12 temporarily stores the computer program to be executed by the processor 11. The RAM 12 temporarily stores the data that is temporarily used by the processor 11 when the processor 11 executes the computer program. The RAM 12 may be, for example, a D-RAM (Dynamic RAM).

The ROM 13 stores the computer program to be executed by the processor 11. The ROM 13 may otherwise store fixed data. The ROM 13 may be, for example, a P-ROM (Programmable ROM).

The storage apparatus 14 stores the data that is stored for a long term by the bioanalysis system 10. The storage apparatus 14 may operate as a temporary storage apparatus of the processor 11. The storage apparatus 14 may include, for example, at least one of a hard disk apparatus, a magneto-optical disk apparatus, a SSD (Solid State Drive), and a disk array apparatus.

The input apparatus 15 is an apparatus that receives an input instruction from a user of the bioanalysis system 10. The input apparatus 15 may include, for example, at least one of a keyboard, a mouse, and a touch panel. The input apparatus 15 may be a dedicated controller (operation terminal). The input apparatus 15 may also include a terminal owned by the user (e.g., a smartphone, a tablet terminal, etc.). The input apparatus 15 may be an apparatus that allows an audio input including a microphone, for example.

The output apparatus 16 is an apparatus that outputs information about the bioanalysis system 10 to the outside. For example, the output apparatus 16 may be a display apparatus (e.g., a display) that is configured to display the information about the bioanalysis system 10. The display apparatus here may be a TV monitor, a personal computer monitor, a smartphone monitor, a tablet terminal monitor, or another portable terminal monitor. The display apparatus may be a large monitor or a digital signage installed in various facilities such as stores. The output apparatus 16 may be an apparatus that outputs the information in a format other than an image. For example, the output apparatus 16 may be a speaker that audio-outputs the information about the bioanalysis system 10.
(Functional Configuration)
Next, with reference to FIG. 2, a functional configuration of the bioanalysis system 10 according to the first example embodiment will be described. FIG. 2 is a block diagram illustrating the functional configuration of the bioanalysis system according to the first example embodiment.

Figure 2:
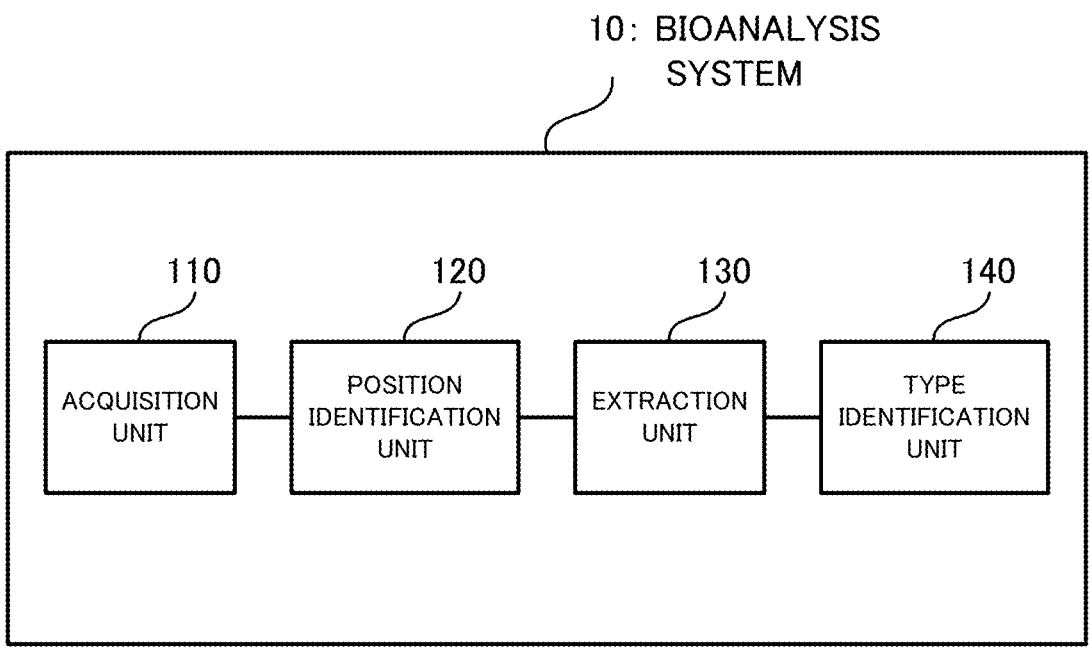
FIG. 2 is a block diagram illustrating a functional configuration of the bioanalysis system according to the first example embodiment.

As illustrated in FIG. 2, the bioanalysis system 10 according to the first example embodiment includes, as processing blocks for realizing the functions thereof, an acquisition unit 110, a position identification unit 120, an extraction unit 130, and a type identification unit 140. Each of the acquisition unit 110, the position identification unit 120, the extraction unit 130, and the type identification unit 140 may be realized or implemented by the processor 11 (see FIG. 1).

The acquisition unit 110 is configured to obtain a plurality of two-dimensional data with different depths in the skin of a living body. The acquisition unit 110 may use optical coherence tomography (OCT) to obtain the plurality of two-dimensional data. The number of the plurality of two-dimensional data may be two, or three or more. The plurality of two-dimensional data obtained by the acquisition unit 110 are configured to be outputted to the position identification unit 120.

The position identification unit 120 identifies a position of a pore part (e.g., a pore, a sweat gland, etc.) in the skin of a living body, on the basis of at least one of the two-dimensional data obtained by the acquisition unit 110. When the two-dimensional data include a plurality of pore parts, the position identification unit 120 may identify the position of each of the plurality of pore parts. A detailed description of a specific method of identifying the position of the pore part from the two-dimensional data will be omitted here, because the existing techniques/technologies can be applied to the method, as appropriate. The position identification unit 120 may identify the position of the pore part in each of the different depths, by using the plurality of two-dimensional data. The position identification unit 120 may identify (in other words, estimate) the position of the pore part with a depth that is not included in the plurality of two-dimensional data, on the basis of the plurality of two-dimensional data. Information about the position of the pore part identified by the position identification unit 120 is configured to be outputted to the extraction unit 130.

The extraction unit 130 is configured to extract a diameter of the pore part from each of the plurality of two-dimensional data. For example, when the acquisition unit 110 obtains two two-dimensional data (first two-dimensional data and second two-dimensional data), the extraction unit 130 extracts each of the diameter of the pore part in the first two-dimensional data and the diameter of the pore part in the second two-dimensional data. When the two-dimensional data include a plurality of pore parts, the extraction unit 130 may extract the diameter for each of the plurality of pore parts. A detailed description of a specific method of extracting the diameter of the pore part from the two-dimensional data will be omitted here, because the existing techniques/technologies can be applied to the method, as appropriate. Information about the diameter of the pore part extracted by the extraction unit 130 is configured to be outputted to the type identification unit 140.

The type identification unit 140 is configured to identify a type of the pore part on the basis of the diameter of the pore part extracted by the extraction unit 130. The type identification unit 140 identifies the type of the pore part, for example, by using properties of the diameter corresponding to the type of the pore part. A specific method of identifying the type of the pore part will be described in detail in another example embodiment later.

(Flow of Operation)

Next, with reference to FIG. 3, a flow of operation of the bioanalysis system 10 according to the first example embodiment will be described. FIG. 3 is a flowchart illustrating the flow of the operation of the bioanalysis system according to the first example embodiment.

Figure 3:
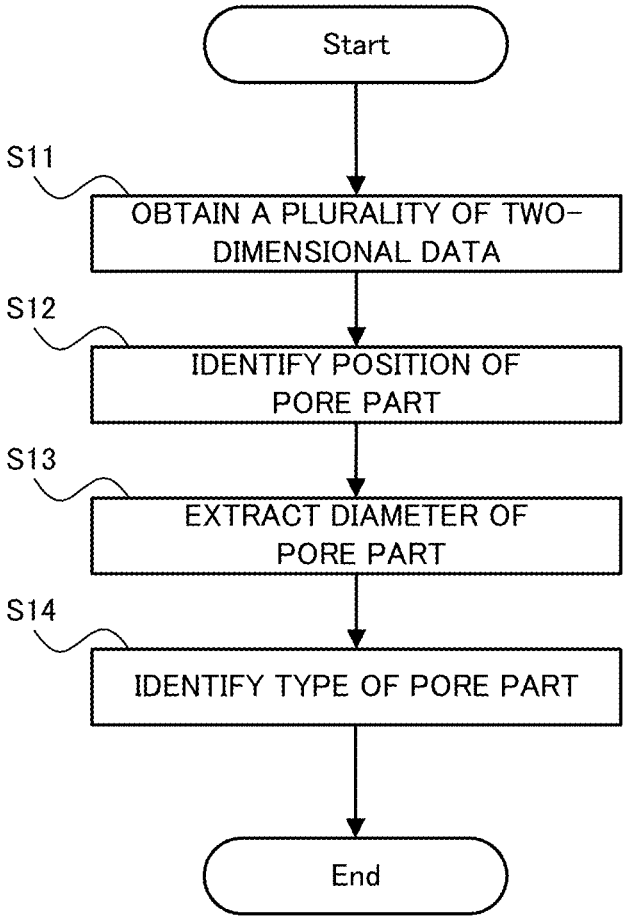
FIG. 3 is a flowchart illustrating a flow of operation of the bioanalysis system according to the first example embodiment.

As illustrated in FIG. 3, when the operation of the bioanalysis system 10 according to the first example embodiment is started, first, the acquisition unit 110 obtains a plurality of two-dimensional data with different depths in the skin of a living body (step S11). Subsequently, the position identification unit 120 identifies the position of the pore part in the skin of the living body, on the basis of at least one of the two-dimensional data obtained by the acquisition unit 110 (step S12). Subsequently, the extraction unit 130 extracts the diameter of the pore part from each of the plurality of two-dimensional data obtained by the acquisition unit 110 (step S13). Subsequently, the type identification unit 140 identifies the type of the pore part on the basis of the diameter of the pore part extracted by the extraction unit 130 (step S14).

When the plurality of two-dimensional data include a plurality of pore parts, the step S12 to the step S14 may be performed simultaneously in parallel for each pore part. Alternatively, the step S12 to the step S14 may be looped a plurality of times while changing a target pore part.

Technical Effect

Next, a technical effect obtained by the bioanalysis system 10 according to the first example embodiment will be described.

As described in FIG. 1 to FIG. 3, in the bioanalysis system 10 according to the first example embodiment, a plurality of two-dimensional data with different depths are used. In addition, the diameter of the pore part is extracted from each of the plurality of two-dimensional data. In this way, it is possible to properly identify the position and the type of the pore part in the skin of a living body

Second Example Embodiment

The bioanalysis system 10 according to a second example embodiment will be described with reference to FIG. 4 and FIG. 5. The second example embodiment is partially different from the first example embodiment only in the configuration and operation, and may be the same as the first example embodiment in the hardware configuration (see FIG. 1) or the like, for example. For this reason, a part that is different from the first example embodiment will be described in detail below, and a description of other overlapping parts will be omitted as appropriate.

(Functional Configuration)

First, with reference to FIG. 4, a functional configuration of the bioanalysis system 10 according to the second example embodiment will be described. FIG. 4 is a block diagram illustrating the functional configuration of the bioanalysis system according to the second example embodiment. In FIG. 4, the same components as those illustrated in FIG. 2 carry the same reference numerals.

Figure 4:
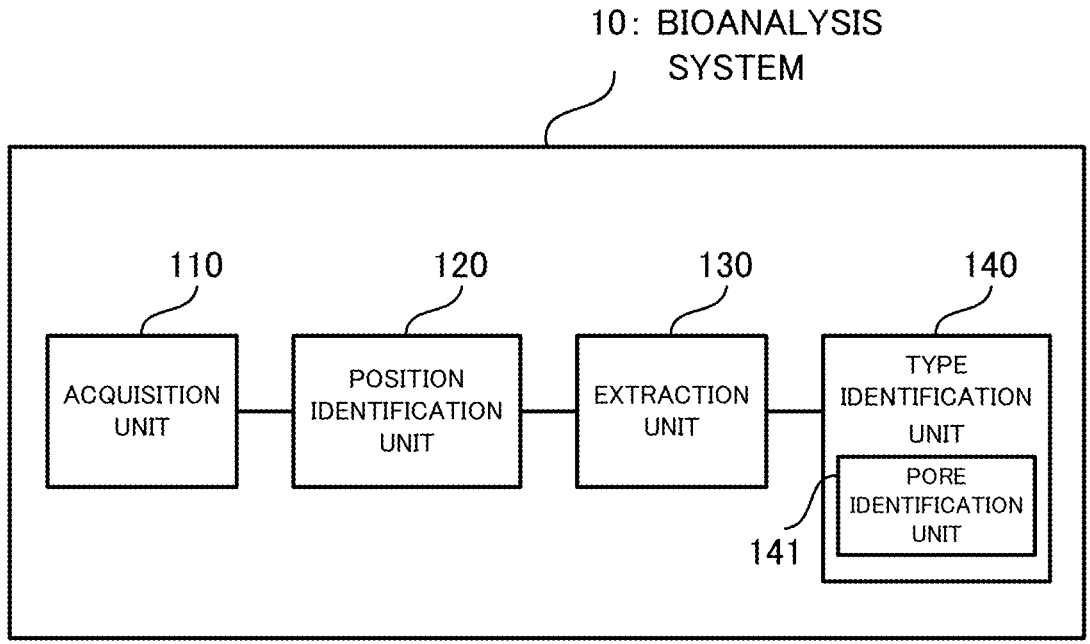
FIG. 4 is a block diagram illustrating a functional configuration of a bioanalysis system according to a second example embodiment.

As illustrated in FIG. 4, the bioanalysis system 10 according to the second example embodiment includes, as processing blocks for realizing the functions thereof, the acquisition unit 110, the position identification unit 120, the extraction unit 130, and the type identification unit 140. In particular, the type identification unit 140 according to the second example embodiment includes a pore identification unit 141. The pore identification unit 141 may be realized or implemented by the processor 11 (see FIG. 1).

The pore identification unit 141 is configured to identify that the type of the pore part is a pore. The pore identification unit 141 may be configured to determine whether the type of the pore part is a pore or other than the pore. A specific method of identifying that the type of the pore part is a pore will be described in detail in another example embodiments later.

(Flow of Operation)

Next, with reference to FIG. 5, a flow of operation of the bioanalysis system 10 according to the second example embodiment will be described. FIG. 5 is a flowchart illustrating the flow of the operation of the bioanalysis system according to the second example embodiment. In FIG. 5, the same steps as those illustrated in FIG. 3 carry the same reference numerals.

Figure 5:
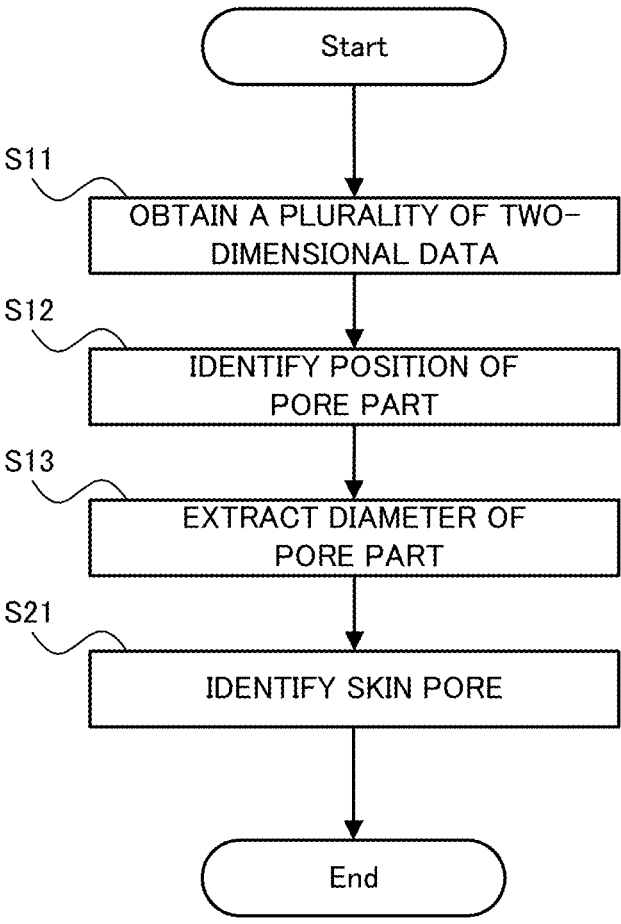
FIG. 5 is a flowchart illustrating a flow of operation of the bioanalysis system according to the second example embodiment.

As illustrated in FIG. 5, when the operation of the bioanalysis system 10 according to the second example embodiment is started, first, the acquisition unit 110 obtains a plurality of two-dimensional data with different depths in the skin of a living body (step S11). Subsequently, the position identification unit 120 identifies the position of the pore part in the skin of the living body, on the basis of at least one of the two-dimensional data obtained by the acquisition unit 110 (step S12). Subsequently, the extraction unit 130 extracts the diameter of the pore part from each of the plurality of two-dimensional data obtained by the acquisition unit 110 (step S13). Subsequently, the pore identification unit 141 performs a process for identifying that the pore part is a pore, on the basis of the diameter of the pore part extracted by the extraction unit 130 (step S21). The type identification unit 140 may perform a process for identifying a type other than the pore, for the pore part that is not identified as a pore by the pore identification unit 141. For example, the pore part that is not identified as a pore, may be identified as a sweat gland, by combining configurations in fourth and fifth example embodiments described later.

Technical Effect

Next, a technical effect obtained by the bioanalysis system 10 according to the second example embodiment will be described.

As described in FIG. 4 and FIG. 5, according to the bioanalysis system 10 in the second example embodiment, it is possible to identify that the type of the pore part is a pore 310, on the basis of a plurality of two-dimensional data with different depths (especially, the diameter of the pore part extracted from the plurality of two-dimensional data). If the pore part can be identified as the pore 310, for example, it is possible to extract only the pore 310 from among a plurality of pore parts including other than the pore 310 and to perform various processes. Alternatively, it is also possible to exclude only the pore 310 from among a plurality of pore parts including other than the pore 310 and to perform various processes.

Third Example Embodiment

The bioanalysis system 10 according to a third example embodiment will be described with reference to FIG. 6 to FIG. 9. The third example embodiment is partially different from the second example embodiment only in the configuration and operation, and may be the same as the first and second example embodiments in the other parts. For this reason, a part that is different from the first and second example embodiments will be described in detail below, and a description of other overlapping parts will be omitted as appropriate.

(Functional Configuration)

Figure 6:
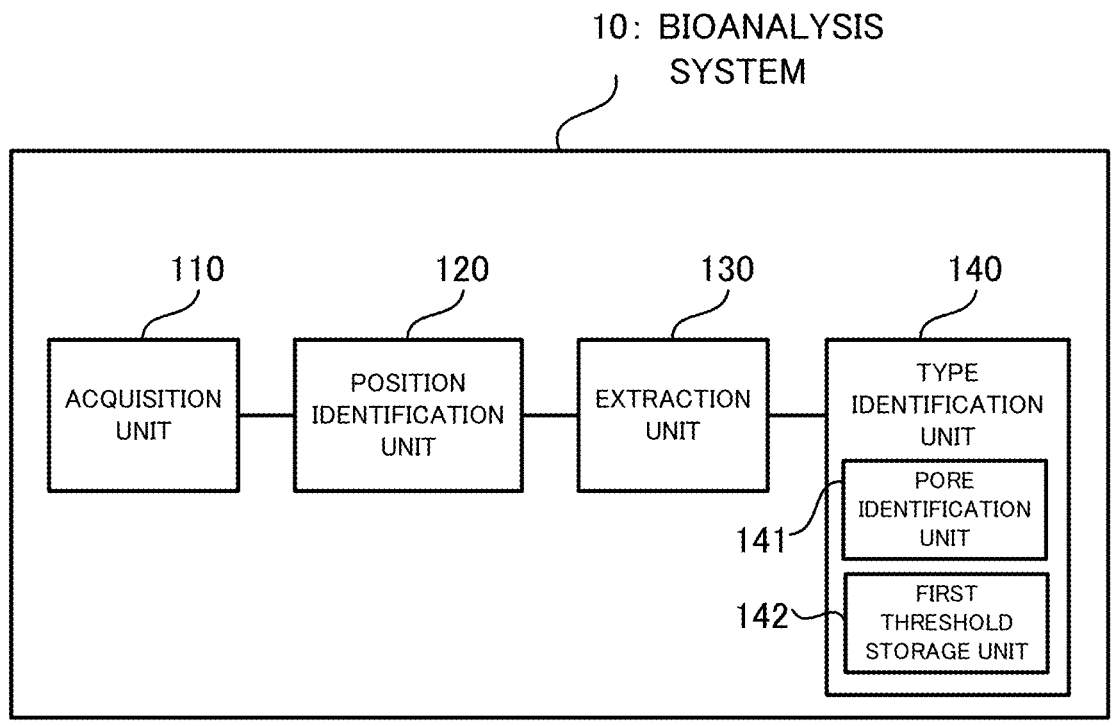
FIG. 6 is a block diagram illustrating a functional configuration of a bioanalysis system according to a third example embodiment.

First, with reference to FIG. 6, a functional configuration of the bioanalysis system 10 according to the third example embodiment will be described. FIG. 6 is a block diagram illustrating the functional configuration of the bioanalysis system according to the third example embodiment. In FIG. 6, the same components as those illustrated in FIG. 4 carry the same reference numerals.

As illustrated in FIG. 6, the bioanalysis system 10 according to the third example embodiment includes, as processing blocks for realizing the functions thereof, the acquisition unit 110, the position identification unit 120, the extraction unit 130, and the type identification unit 140. In particular, the type identification unit 140 according to the third example embodiment includes the pore identification unit 141 and a first threshold storage unit 142. That is, the type identification unit 140 according to the third example embodiment further includes the first threshold storage unit 142, in addition to the configuration in the second example embodiment (see FIG. 4). The first threshold storage unit 142 may be realized or implemented by the storage apparatus 14 (see FIG. 1).

The first threshold storage unit 142 is configured to store a first threshold used in the identification of the type of the pore part. The first threshold is a threshold for identifying that the type of the pore part is a pore, and is set in advance as a value corresponding to a change rate of the diameter of the pore part. For the first threshold, an appropriate value may be determined on the basis of results of prior experiments, for example. A setting example of the first threshold will be described in detail in the following description of the diameter of the pore.

(Diameter of Pore)

Figure 7:
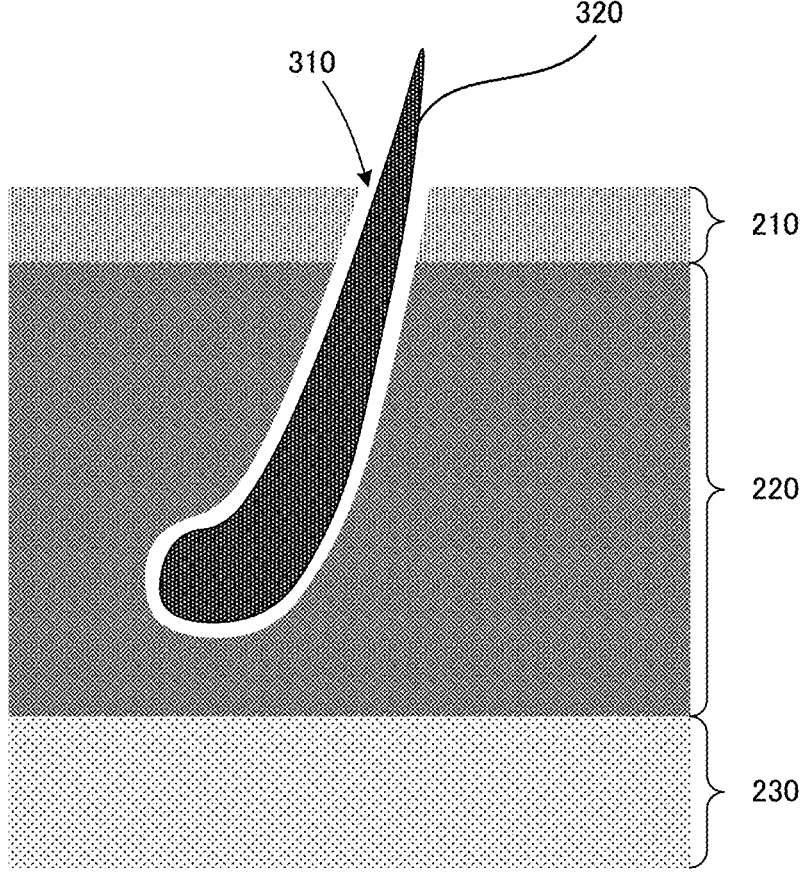
FIG. 7 is a cross-sectional view illustrating an example of a shape of a pore in the skin.
Figure 8:
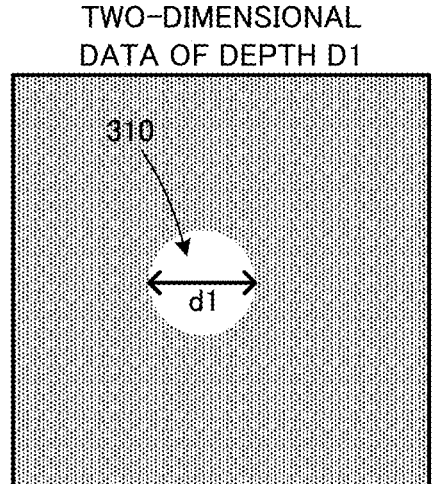
FIG. 8 is a plan view illustrating an example of two-dimensional data with different depths including pores.
Figure 8:
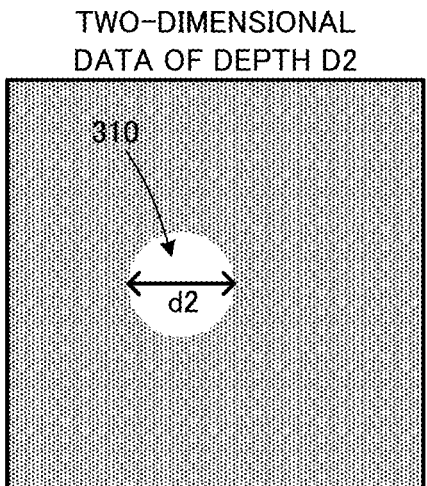

Next, the pore identified by the bioanalysis system 10 according to the third example embodiment will be described in detail with reference to FIG. 7 and FIG. 8. FIG. 7 is a cross-sectional view illustrating an example of a shape of the pore in the skin. FIG. 8 is a plan view illustrating an example of two-dimensional data with different depths including pores.

As illustrated in FIG. 7, there are an epidermis 210, a dermis 220, and a subcutaneous fat 230 near a skin surface of a living body in this order from the surface side. Then, there is a pore 310 in the epidermis 210 and the dermis 220, and a hair 320 is grown in a direction from the dermis 220 to the epidermis 210.

Here, in particular, the diameter of the pore 310 varies to some extent depending on the depth, but the change rate thereof is relatively small (e.g., it is clearly small in comparison with the change rate of the diameter of a sweat gland 410 described later (see FIG. 13 and FIG. 14, etc.)). More specifically, for example, in the case of downy hair on a face, the diameter of a hair bulb part is about 100 μm and the diameter of the other part is about 0.01 mm (i.e., 10 μm), and it changes gradually continuously. Therefore, if the first threshold is set on the basis of such a value, it is possible to identify whether the pore part is the pore 310, depending on whether or not the change rate of the diameter of the pore part is less than or equal to the first threshold.

As illustrated in FIG. 8, it is assumed that the two-dimensional data including the pore 310 are obtained at depths D1 and D2. In this case, there is no significant difference between a diameter d1 of the pore in the two-dimensional data with the depth D1 and a diameter d2 of the pore part in the two-dimensional data with the depth D2. Therefore, the change rate of the diameter obtained from the diameters d1 and d2 is relatively small. Therefore, the change rate of the diameter is less than or equal to the first threshold. As a result, even if the type of the pore 310 illustrated in the figure is unknown, the pore part can be identified as the pore 310.

(Flow of Operation)

Figure 9:
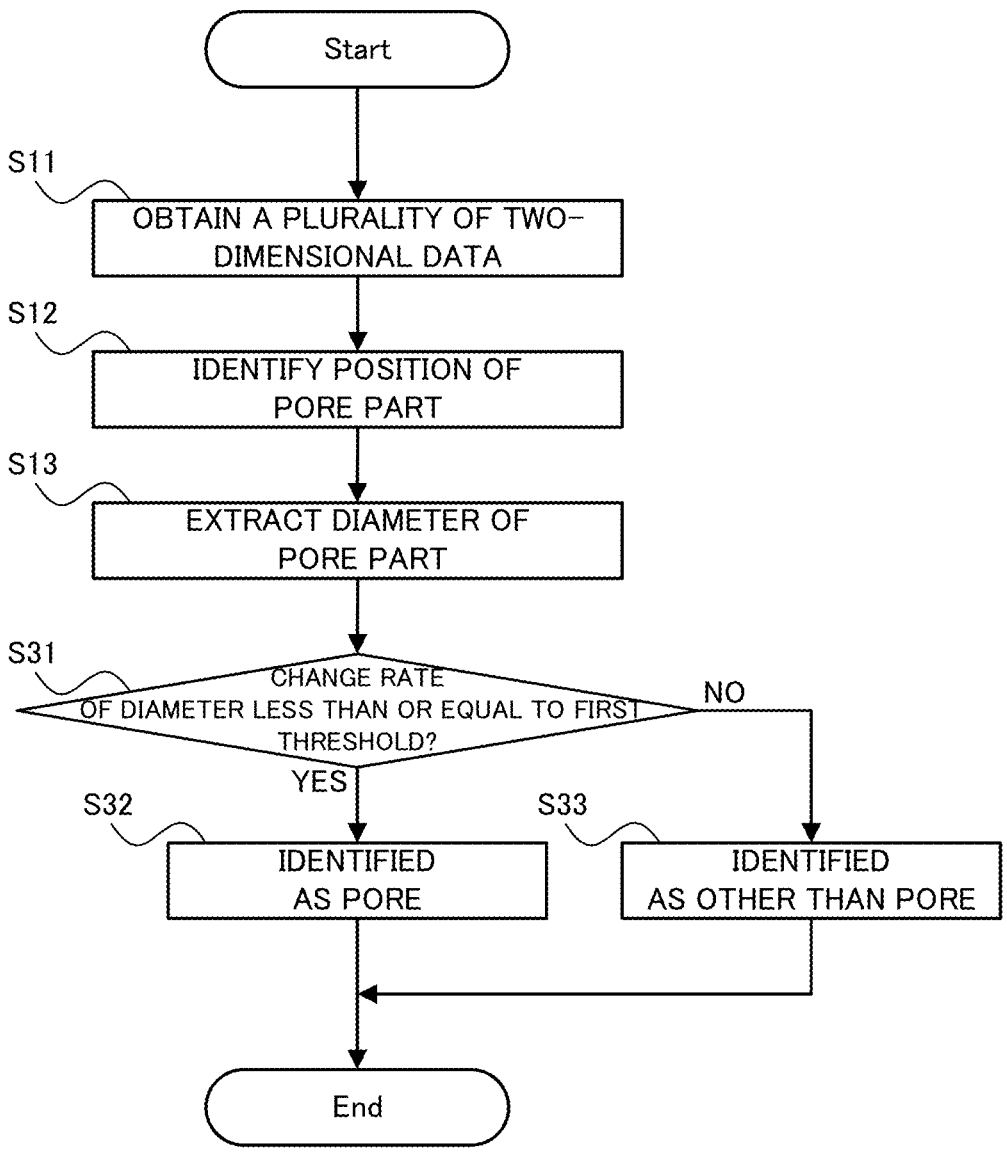
FIG. 9 is a flowchart illustrating a flow of operation of the bioanalysis system according to the third example embodiment.

Next, with reference to FIG. 9, a flow of operation of the bioanalysis system 10 according to the third example embodiment will be described. FIG. 9 is a flowchart illustrating the flow of the operation of the bioanalysis system according to the third example embodiment. In FIG. 9, the same steps as those illustrated in FIG. 3 carry the same reference numerals.

As illustrated in FIG. 9, when the operation of the bioanalysis system 10 according to the third example embodiment is started, first, the acquisition unit 110 obtains a plurality of two-dimensional data with different depths in the skin of a living body (step S11). Subsequently, the position identification unit 120 identifies the position of the pore part in the skin of the living body, on the basis of at least one of the two-dimensional data obtained by the acquisition unit 110 (step S12). Subsequently, the extraction unit 130 extracts the diameter of the pore part from each of the plurality of two-dimensional data obtained by the acquisition unit 110 (step S13).

Subsequently, the pore identification unit 141 calculates the change rate of the diameter of the pore part, and determines whether or not the change rate is less than or equal to the first threshold stored in the first threshold storage unit 142 (step S31). When the change rate of the pore part is less than or equal to the first threshold (step S31: YES), the pore identification unit 141 identifies that the type of the pore part is a pore (step S32). On the other hand, when the change rate of the pore part is not less than or equal to the first threshold (step S31: NO), the pore identification unit 141 identifies that the type of the pore part is other than a pore (step S33).

Technical Effect

Next, a technical effect obtained by the bioanalysis system 10 according to the third example embodiment will be described.

As described in FIG. 6 to FIG. 9, in the bioanalysis system 10 according to the third example embodiment, the type of the pore part is identified by comparing the change rate of the diameter of the pore part with the first threshold. In this way, it is possible to properly identify that the type of the pore part is the pore 310, by using characteristics of the pore 310 in which the change rate of the diameter is relatively small.

Fourth Example Embodiment

The bioanalysis system 10 according to a fourth example embodiment will be described with reference to FIG. 10 and FIG. 11. The fourth example embodiment is partially different from the first to third example embodiments only in the configuration and operation, and may be the same as the first to third example embodiments in the other parts. For this reason, a part that is different from each of the example embodiments described above will be described in detail below, and a description of other overlapping parts will be omitted as appropriate.

(Functional Configuration)

First, with reference to FIG. 10, a functional configuration of the bioanalysis system 10 according to the fourth example embodiment will be described. FIG. 10 is a block diagram illustrating the functional configuration of the bioanalysis system according to the fourth example embodiment. In FIG. 10, the same components as those illustrated in FIG. 2 carry the same reference numerals.

Figure 10:
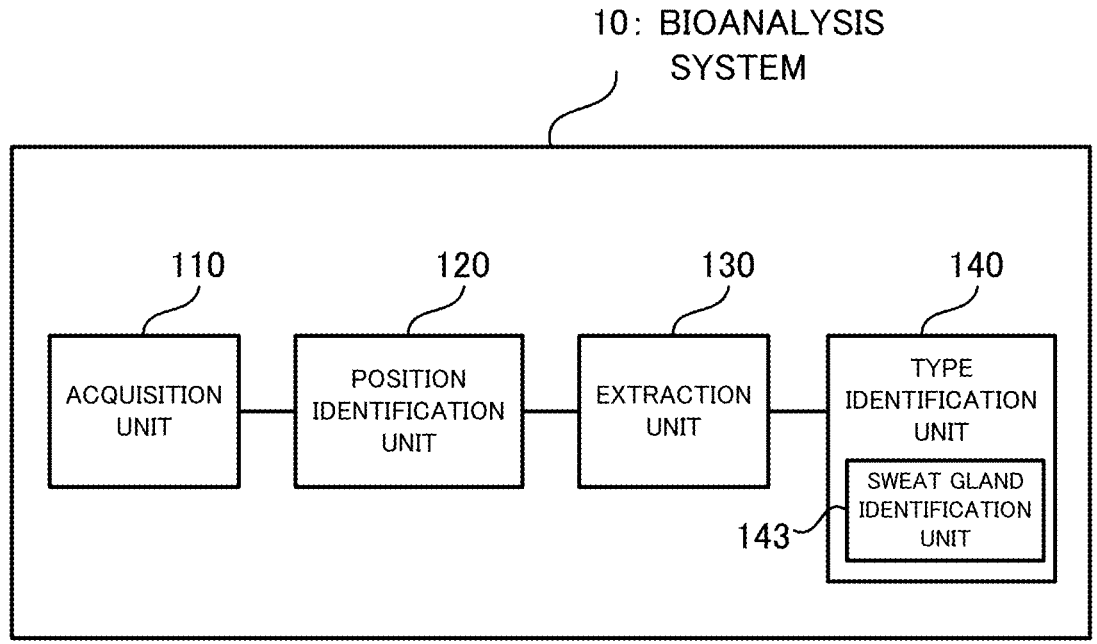
FIG. 10 is a block diagram illustrating a functional configuration of a bioanalysis system according to a fourth example embodiment.

As illustrated in FIG. 10, the bioanalysis system 10 according to the fourth example embodiment includes, as processing blocks for realizing the functions thereof, the acquisition unit 110, the position identification unit 120, the extraction unit 130, and the type identification unit 140. In particular, the type identification unit 140 according to the fourth example embodiment includes the sweat gland identification unit 143. The sweat gland identification unit 143 may be realized or implemented by the processor 11 (see FIG. 1).

The sweat gland identification unit 143 is configured to identify that the type of the pore part is a sweat gland. The sweat gland identification unit 143 may be configured to determine whether the type of the pore part is a sweat gland or other than the sweat gland. A specific method of identifying that the type of the pore part is a sweat gland will be described in detail in another example embodiment later.

(Flow of Operation)

Next, with reference to FIG. 11, a flow of operation of the bioanalysis system 10 according to the fourth example embodiment will be described. FIG. 11 is a flowchart illustrating the flow of the operation of the bioanalysis system according to the fourth example embodiment. In FIG. 11, the same steps as those illustrated in FIG. 3 carry the same reference numerals.

Figure 11:
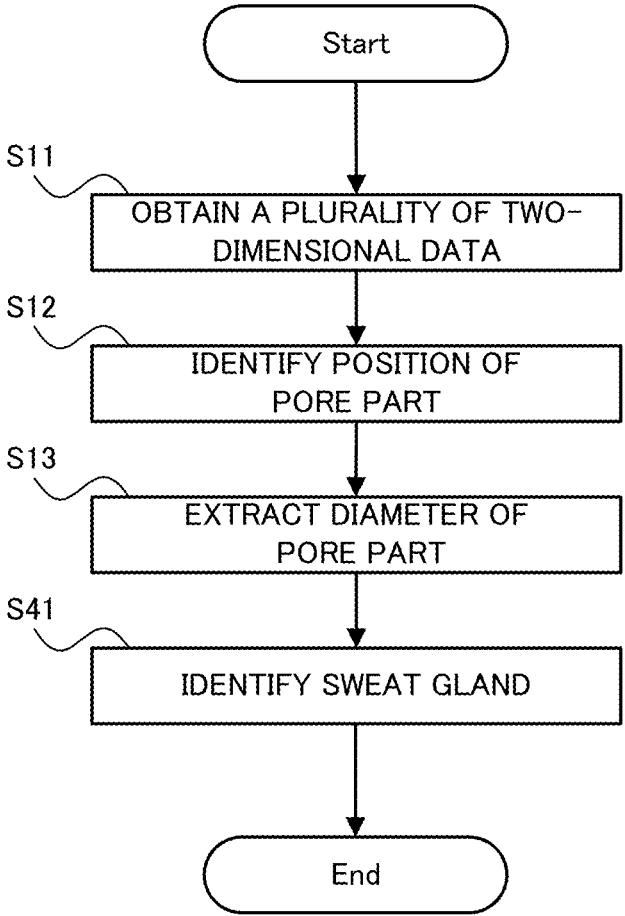
FIG. 11 is a flowchart illustrating a flow of operation of the bioanalysis system according to the fourth example embodiment.

As illustrated in FIG. 11, when the operation of the bioanalysis system 10 according to the fourth example embodiment is started, first, the acquisition unit 110 obtains a plurality of two-dimensional data with different depths in the skin of a living body (step S11). Subsequently, the position identification unit 120 identifies the position of the pore part in the skin of the living body, on the basis of at least one of the two-dimensional data obtained by the acquisition unit 110 (step S12). Subsequently, the extraction unit 130 extracts the diameter of the pore part from each of the plurality of two-dimensional data obtained by the acquisition unit 110 (step S13). Subsequently, the sweat gland identification unit 143 performs a process for identifying that the pore part is a sweat gland, on the basis of the diameter of the pore part extracted by the extraction unit 130 (step S41). The type identification unit 140 may perform the process for identifying that the type other than the sweat gland, on the basis of the pore part that is not identified as the sweat gland in the sweat gland identification unit 143. For example, the configuration in the second and third example embodiments may be combined to identify that the pore part that is not identified as the sweat gland is a pore.

Technical Effect

Next, a technical effect obtained by the bioanalysis system 10 according to the fourth example embodiment will be described.

As described in FIG. 10 and FIG. 11, according to the bioanalysis system 10 in the fourth example embodiment, it is possible to identify that the type of the pore part is a sweat gland 410, on the basis of a plurality of two-dimensional data with different depths (especially, the diameter of the pore part extracted from the plurality of two-dimensional data). If the pore part can be identified as the sweat gland 410, for example, it is possible to extract only the sweat gland 410 from among a plurality of pore parts including other than the sweat gland 410 and to perform various processes. Alternatively, it is also possible to exclude only the sweat gland 410 from among a plurality of pore parts including other than the sweat gland 410 and to perform various processes.

Fifth Example Embodiment

The bioanalysis system 10 according to a fifth example embodiment will be described with reference to FIG. 12 to FIG. 15. The fifth example embodiment is partially different from the fourth example embodiment only in the configuration and operation, and may be the same as the fourth example embodiment in the other parts. For this reason, a part that is different from each of the example embodiments described above will be described in detail below, and a description of other overlapping parts will be omitted as appropriate.

(Functional Configuration)

Figure 12:
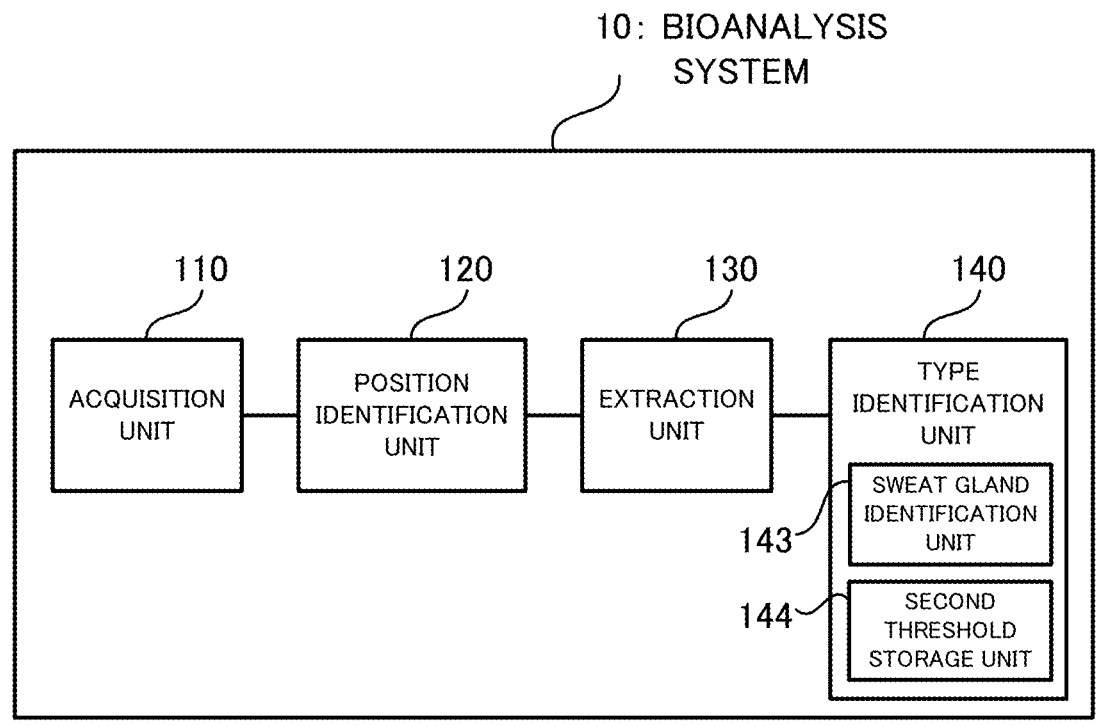
FIG. 12 is a block diagram illustrating a functional configuration of a bioanalysis system according to a fifth example embodiment.

First, with reference to FIG. 12, a functional configuration of the bioanalysis system 10 according to the fifth example embodiment will be described. FIG. 12 is a block diagram illustrating the functional configuration of the bioanalysis system according to the fifth example embodiment. In FIG. 12, the same components as those illustrated in FIG. 10 carry the same reference numerals.

As illustrated in FIG. 12, the bioanalysis system 10 according to the fifth example embodiment includes, as processing blocks for realizing the functions thereof, the acquisition unit 110, the position identification unit 120, the extraction unit 130, and the type identification unit 140. In particular, the type identification unit 140 according to the fifth example embodiment includes the sweat gland identification unit 143 and a second threshold storage unit 144. That is, the type identification unit 140 according to the fifth example embodiment further includes the second threshold storage unit 144, in addition to the configuration in the fourth example embodiment (see FIG. 10). The second threshold storage unit 144 may be realized or implemented by the storage apparatus 14 (see FIG. 1).

The second threshold storage unit 144 is configured to store a second threshold used in the identification of the type of the pore part. The second threshold is a threshold for identifying that the type of the pore part is a sweat gland, and is set in advance as a value corresponding to the change rate of the diameter of the pore part. The second threshold may be set as a threshold for identifying the pore part other than the sweat gland (other than the pore). For the second threshold, an appropriate value may be determined on the basis of results of prior experiment, for example. A setting example of the second threshold will be described in detail in the following description of the diameter of the sweat gland.

(Diameter of Sweat Gland)

Figure 13:
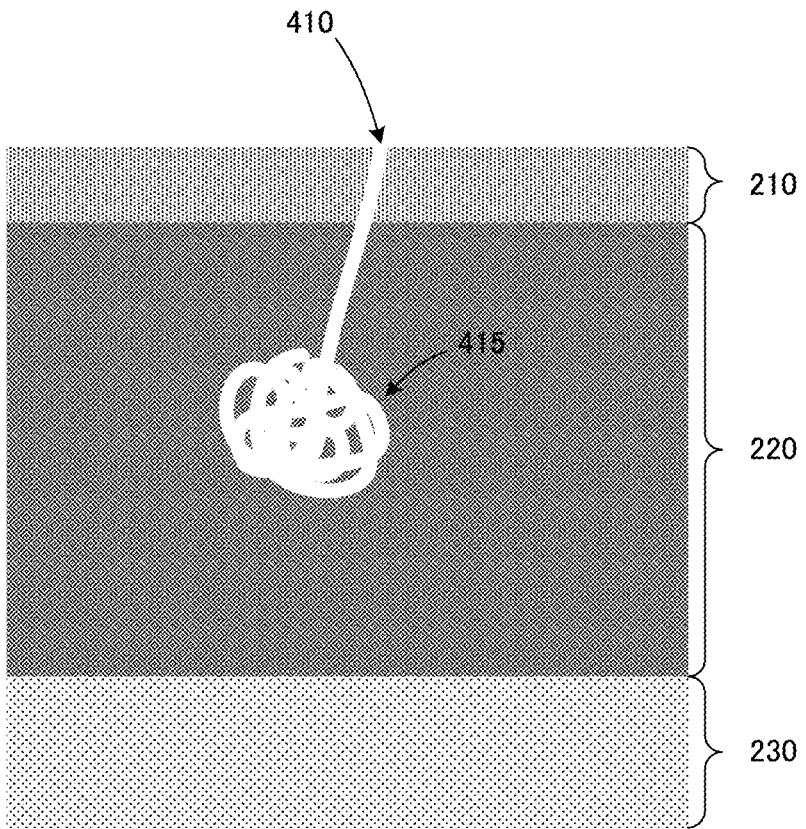
FIG. 13 is a cross-sectional view illustrating an example of a shape of a sweat gland in the skin.
Figure 14:
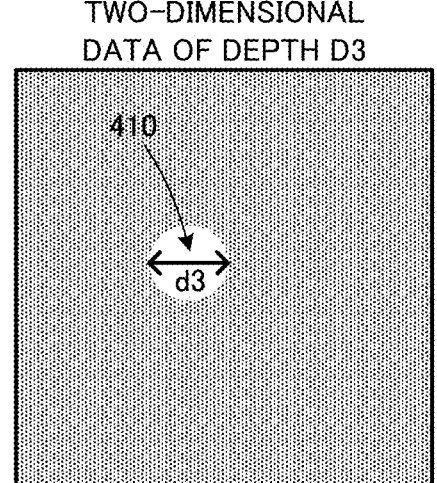
FIG. 14 is a plan view illustrating an example of two-dimensional data with different depths including sweat glands.
Figure 14:
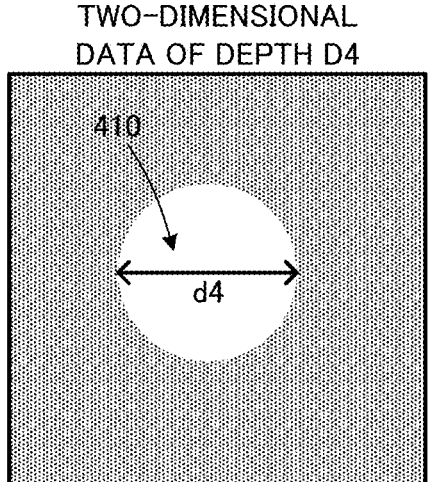

Next, the sweat gland identified by the bioanalysis system 10 according to the fifth example embodiment will be described in detail with reference to FIG. 13 and FIG. 14. FIG. 13 is a cross-sectional view illustrating an example of a shape of the sweat gland in the skin. FIG. 14 is a plan view illustrating an example of two-dimensional data with different depths including sweat glands.

As illustrated in FIG. 13, there are the epidermis 210, the dermis 220, and the subcutaneous fat 230 near a skin surface of a living body in this order from the surface side. Then, there is a sweat gland 410 (e.g., eccrine gland) in the epidermis 210 and the dermis 220.

In particular, the sweat gland 410 includes a coil part 415 as illustrated in the figure. Thus, the diameter of the sweat gland rapidly increases in the coil part 415. Therefore, the change rate of the diameter of the sweat gland 410 is relatively large (e.g., it is clearly large in comparison with the diameter of the pore 310 described above (see FIG. 7 and FIG. 8, etc.)). For example, in the case of the eccrine gland, the diameter of a duct (a part other than the coil part 415) is about 30 to 40 μm, while the diameter of the coil part 415 is about 500 to 700 μm, and it also changes rapidly. Therefore, if the second threshold is set on the basis of such a value, it is possible to identify whether the pore part is the sweat gland 410, depending on whether the change rate of the diameter of the pore part is greater than or equal to the second threshold.

As illustrated in FIG. 14, it is assumed that the two-dimensional data including the sweat gland 410 are obtained at depths D3 and D4. In this case, there is a significant difference between a diameter d3 of the pore in the two-dimensional data in the depth D3 and a diameter d4 of the pore part in the two-dimensional data with the depth D4, due to the coil part 415. Therefore, the change rate of the diameter obtained from the diameters d3 and d4 is relatively large. Therefore, the change rate of the diameter is greater than or equal to the second threshold. As a result, even if the type of the sweat gland 410 illustrated in the figure is unknown, the pore part can be identified as the sweat gland 410.

(Flow of Operation)

Figure 15:
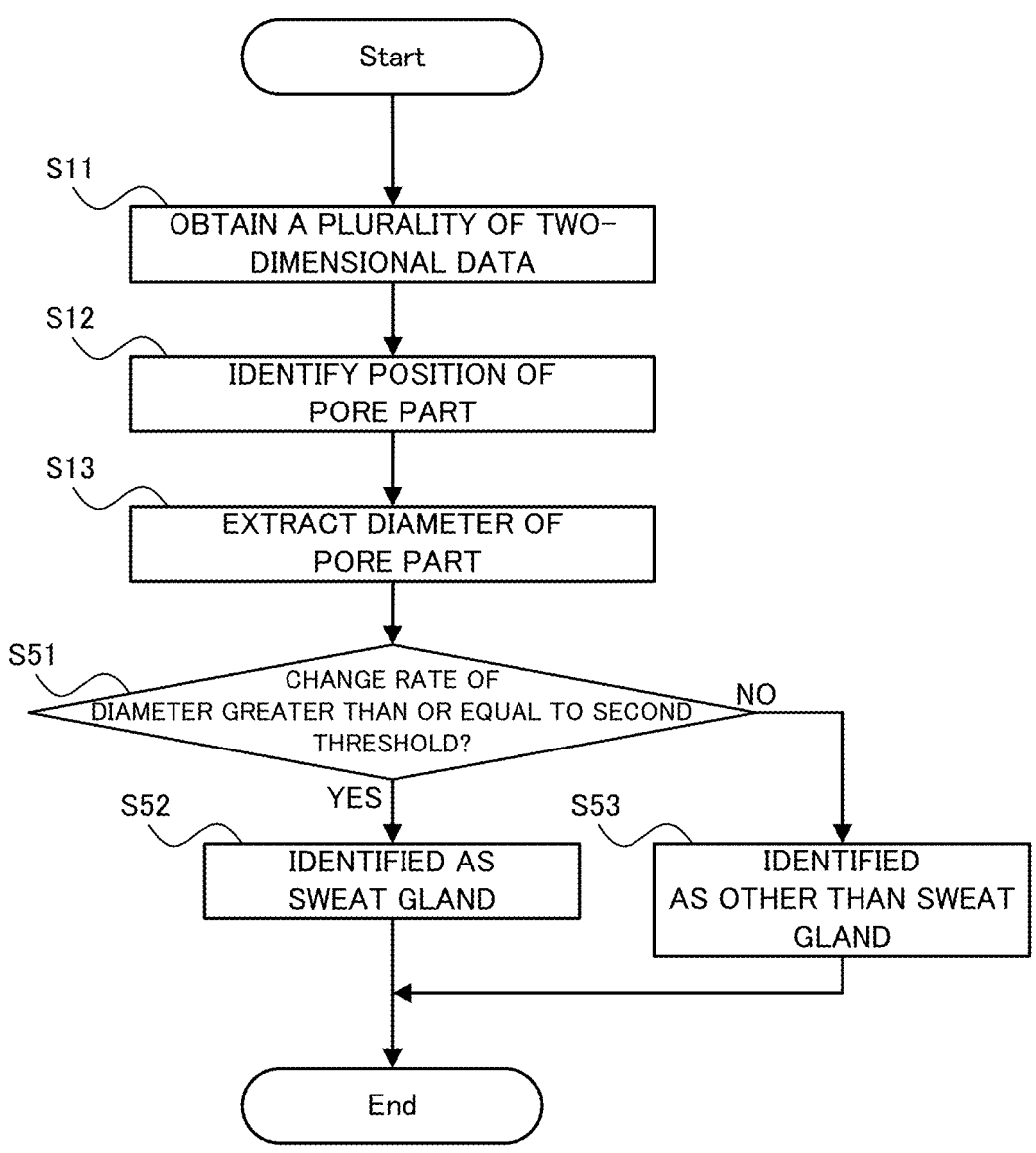
FIG. 15 is a flowchart illustrating a flow of operation of a bioanalysis system according to a fifth example embodiment.

Next, with reference to FIG. 15, a flow of operation of the bioanalysis system 10 according to the fifth example embodiment will be described. FIG. 15 is a flowchart illustrating the flow of the operation of the bioanalysis system according to the fifth example embodiment. In FIG. 15, the same steps as those illustrated in FIG. 3 carry the same reference numerals.

As illustrated in FIG. 15, when the operation of the bioanalysis system 10 according to fifth example embodiment is started, first, the acquisition unit 110 obtains a plurality of two-dimensional data with different depths in the skin of a living body (step S11). Subsequently, the position identification unit 120 identifies the position of the pore part in the skin of the living body, on the basis of at least one of the two-dimensional data obtained by the acquisition unit 110 (step S12). Subsequently, the extraction unit 130 extracts the diameter of the pore part from each of the plurality of two-dimensional data obtained by the acquisition unit 110 (step S13).

Subsequently, the sweat gland identification unit 143 calculates the change rate of the diameter of the pore part, and determines whether or not the change rate is greater than or equal to the second threshold stored in the second threshold storage unit 144 (step S51). When the change rate of the pore part is greater than or equal to the second threshold (step S51: YES), the sweat gland identification unit 143 identifies that the type of the pore part is a sweat gland (step S52). On the other hand, when the change rate of the pore part is not greater than or equal to the second threshold or more (step S51: NO), the sweat gland identification unit 143 identifies that the type of the pore part is other than the sweat gland (step S53).

If the second threshold is set to have the same value as that of the first threshold in the third example embodiment, a comparison with one common threshold makes it possible to identify whether the type of the pore part is the pore 310 or the sweat gland 410. Specifically, when the change rate of the diameter of the pore part is less than or equal to the common threshold, it is possible to identify that the type of the pore part is the pore 310. On the other hand, when the change rate of the diameter of the pore part is greater than or equal to the common threshold, it is possible to identify that the type of the pore part is the sweat gland 410.

Technical Effect

Next, a technical effect obtained by the bioanalysis system 10 according to the fifth example embodiment will be described.

As described in FIG. 12 to FIG. 15, in the bioanalysis system 10 according to the fifth example embodiment, the type of the pore part is identified by comparing the change rate of the diameter of the pore part with the second threshold. In this way, it is possible to properly identify that the type of the pore part is the sweat gland 410, by using the characteristics of the sweat gland 410 in which the change rate of the diameter is relatively large.

The example embodiments up to this point describe the configuration in which each of the pore 310 and the sweat gland 410 is identified as an example of the pore part in the skin of a living body, but a pore part (e.g., a sebaceous gland, etc.) other than the pore 310 and the sweat gland 410 may be identified.

Sixth Example Embodiment

The bioanalysis system 10 according to a sixth example embodiment will be described with reference to FIG. 16 and FIG. 17. The sixth example embodiment is partially different from the first to fifth example embodiments only in the configuration and operation, and may be the same as the first to fifth example embodiments in the other parts. For this reason, a part that is different from each of the example embodiments described above will be described in detail below, and a description of other overlapping parts will be omitted as appropriate.

(Functional Configuration)

First, with reference to FIG. 16, a functional configuration of the bioanalysis system 10 according to the sixth example embodiment will be described. FIG. 16 is a block diagram illustrating the functional configuration of the bioanalysis system according to the sixth example embodiment. In FIG. 16, the same components as those illustrated in FIG. 2 carry the same reference numerals.

Figure 16:
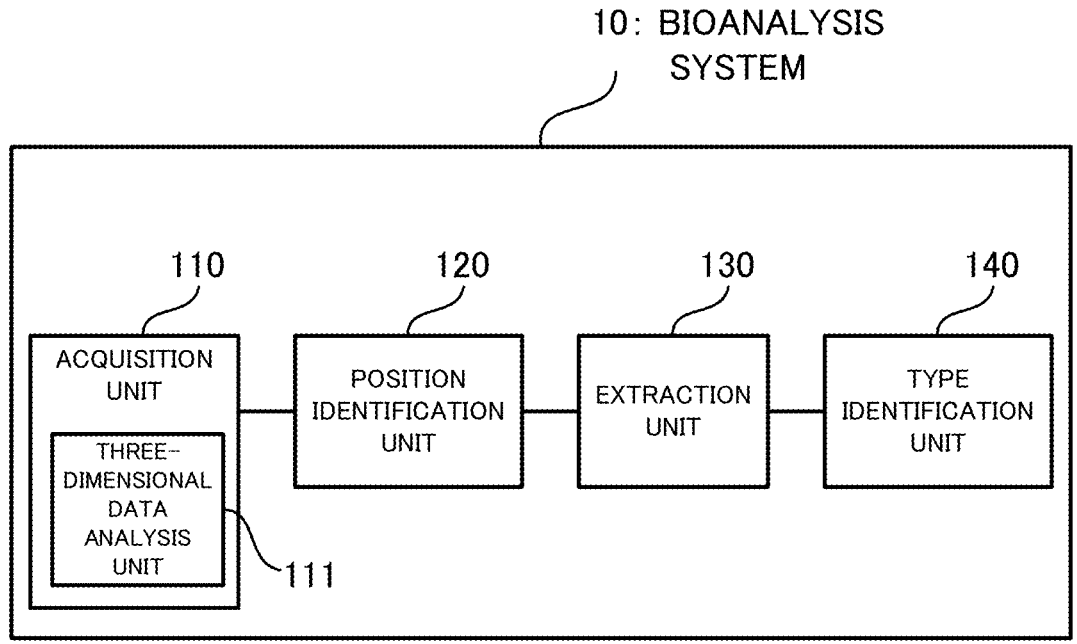
FIG. 16 is a block diagram illustrating a functional configuration of a bioanalysis system according to a sixth example embodiment.

As illustrated in FIG. 16, the bioanalysis system 10 according to the sixth example embodiment includes, as processing blocks for realizing the functions thereof, the acquisition unit 110, the position identification unit 120, the extraction unit 130, and the type identification unit 140. In particular, the acquisition unit 110 according to the sixth example embodiment includes a three-dimensional data analysis unit 111. The three-dimensional data analysis unit 111 may be realized or implemented by the processor 11 (see FIG. 1).

The three-dimensional data analysis unit 111 is configured to obtain a plurality of two-dimensional data with different depths, by analyzing three-dimensional tomographic data about the skin of a living body. The three-dimensional tomographic data here may be data obtained by optical coherence tomography, for example. A detailed description of a specific method of obtaining the plurality of two-dimensional data from the three-dimensional tomographic data will be omitted here, because the existing techniques/technologies may be applied to the method, as appropriate.

(Flow of Operation)

Next, with reference to FIG. 17, a flow of operation of the bioanalysis system 10 according to the sixth example embodiment will be described. FIG. 17 is a flowchart illustrating the flow of the operation of the bioanalysis system according to the sixth example embodiment. In FIG. 17, the same steps as those illustrated in FIG. 3 carry the same reference numerals.

Figure 17:
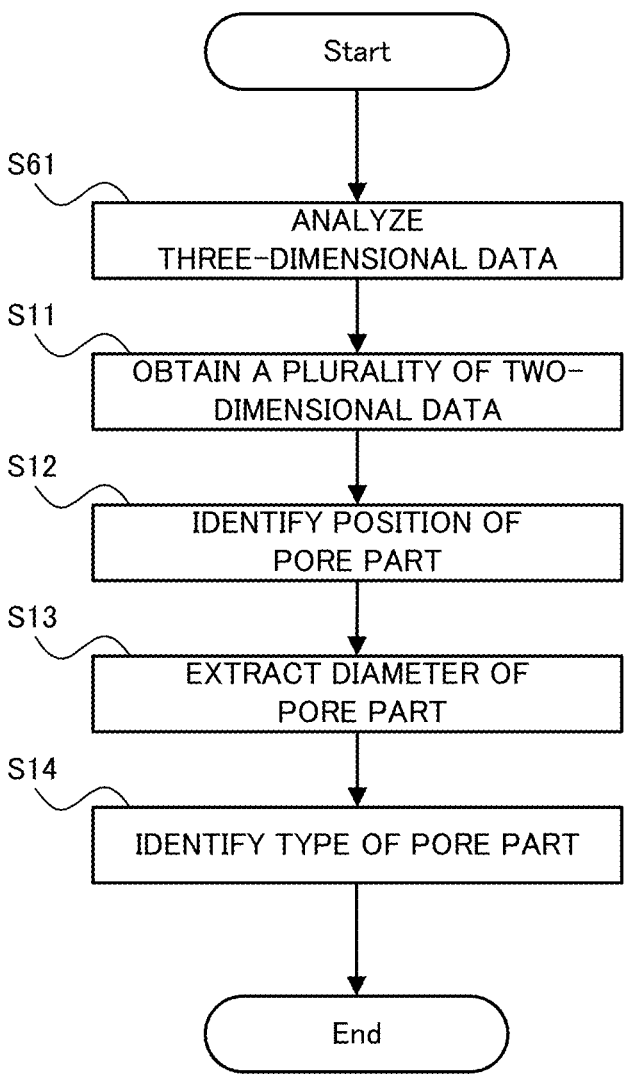
FIG. 17 is a flowchart illustrating a flow of operation of the bioanalysis system according to the sixth example embodiment.

As illustrated in FIG. 17, when the operation of the bioanalysis system 10 according to the sixth example embodiment is started, first, the three-dimensional data analysis unit 111 analyzes the three-dimensional tomographic data (step S61). Through this analysis, the acquisition unit 110 obtains a plurality of two-dimensional data with different depths in the skin of a living body (step S11). Subsequently, the position identification unit 120 identifies the position of the pore part in the skin of the living body, on the basis of at least one of the two-dimensional data obtained by the acquisition unit 110 (step S12). Subsequently, the extraction unit 130 extracts the diameter of the pore part from each of the plurality of two-dimensional data obtained by the acquisition unit 110 (step S13). Subsequently, the type identification unit 140 identifies the type of the pore part on the basis of the diameter of the pore part extracted by the extraction unit 130 (step S14).

Technical Effect

Next, a technical effect obtained by the bioanalysis system 10 according to the sixth example embodiment will be described.

As described with FIG. 10 and FIG. 11, according to the bioanalysis system 10 in the sixth example embodiment, a plurality of two-dimensional data with different depths are obtained from the three-dimensional tomographic data about the skin of a living body. In this way, it is possible to properly identify the position and the type of the pore part included in the three-dimensional tomographic data.

Seventh Example Embodiment

The bioanalysis system 10 according to a seventh example embodiment will be described with reference to FIG. 18 to FIG. 22. The seventh example embodiment is partially different from the first to sixth example embodiments only in the configuration and operation, and may be the same as the first to sixth example embodiments in the other parts. For this reason, a part that is different from each of the example embodiments described above will be described in detail below, and a description of other overlapping parts will be omitted as appropriate.

(Functional Configuration)

Figure 18:
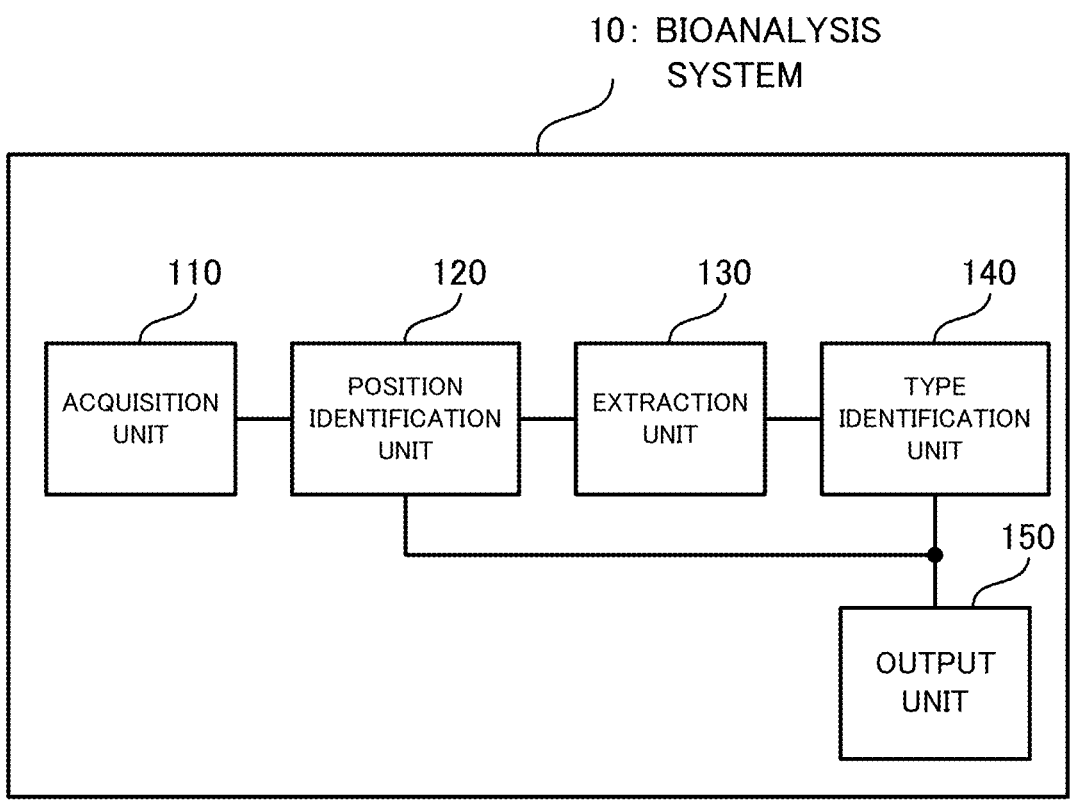
FIG. 18 is a block diagram illustrating a functional configuration of a bioanalysis system according to a seventh example embodiment.

First, with reference to FIG. 18, a functional configuration of the bioanalysis system 10 according to the seventh example embodiment will be described. FIG. 18 is a block diagram illustrating the functional configuration of the bioanalysis system according to the seventh example embodiment. In FIG. 18, the same components as those illustrated in FIG. 2 carry the same reference numerals.

As illustrated in FIG. 18, the bioanalysis system 10 according to the seventh example embodiment includes, as processing blocks for realizing the functions thereof, the acquisition unit 110, the position identification unit 120, the extraction unit 130, the type identification unit 140, and an output unit 150. That is, the bioanalysis system 10 according to the seventh example embodiment further includes the output unit 150, in addition to the configuration in the first example embodiment (see FIG. 2). The output unit 150 may be realized or implemented by the output apparatus 16 (see FIG. 1).

The output unit 150 includes, for example, a display, and is configured to output at least one of a tomography image and a surface image (i.e., an image of an outermost layer) of the skin of a living body including the pore part. The output unit 150 may output the tomography image and the surface image generated by using a plurality of two-dimensional data. Furthermore, when the three-dimensional tomographic data are inputted as in the sixth example embodiment (see FIG. 16 and FIG. 17, etc.), the output unit 150 may output the tomography image and the surface image generated by using the three-dimensional tomographic data. Specific examples the tomography image and the surface image are described in detail later.

(Flow of Operation)

Figure 19:
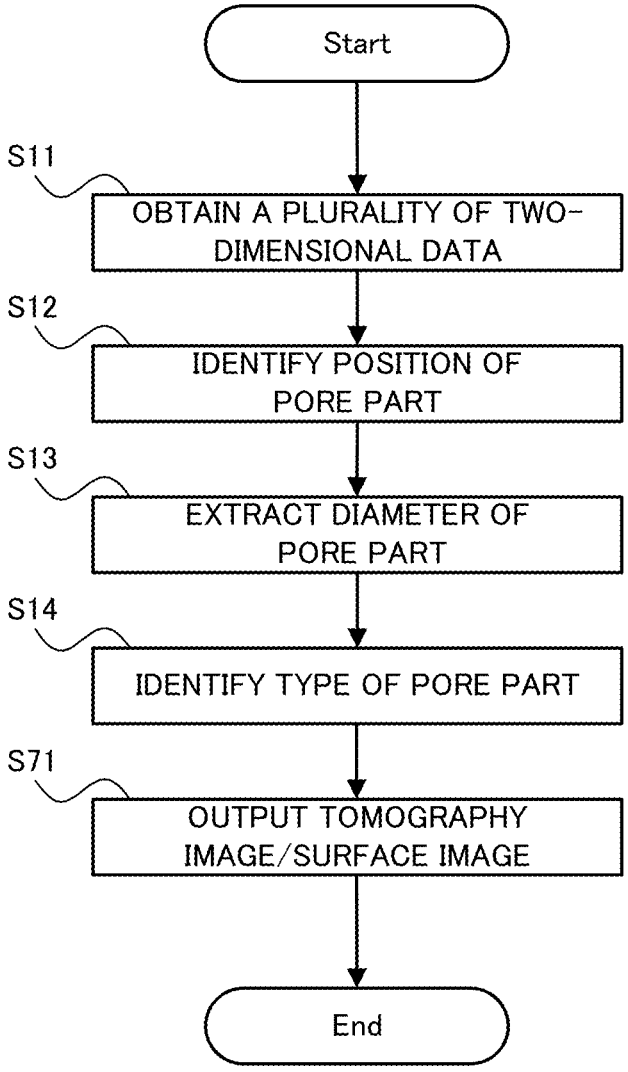
FIG. 19 is a flowchart illustrating a flow of operation of the bioanalysis system according to the seventh example embodiment.

Next, with reference to FIG. 19, a flow of operation of the bioanalysis system 10 according to the seventh example embodiment will be described. FIG. 19 is a flowchart illustrating the flow of the operation of the bioanalysis system according to the seventh example embodiment. In FIG. 19, the same steps as those illustrated in FIG. 3 carry the same reference numerals.

As illustrated in FIG. 19, when the operation of the bioanalysis system 10 according to the seventh example embodiment is started, first, the acquisition unit 110 obtains a plurality of two-dimensional data with different depths in the skin of a living body (step S11). Subsequently, the position identification unit 120 identifies the position of the pore part in the skin of the living body, on the basis of at least one of the two-dimensional data obtained by the acquisition unit 110 (step S12). Subsequently, the extraction unit 130 extracts the diameter of the pore part from each of the plurality of two-dimensional data obtained by the acquisition unit 110 (step S13). Subsequently, the type identification unit 140 identifies the type of the pore part on the basis of the diameter of the pore part extracted by the extraction unit 130 (step S14). Finally, the output unit 150 outputs at least one of the tomography image and the surface image of the skin of the living body, on the basis of the position and the type of the pore part (step S71).

(Specific Output Examples)

Figure 20:
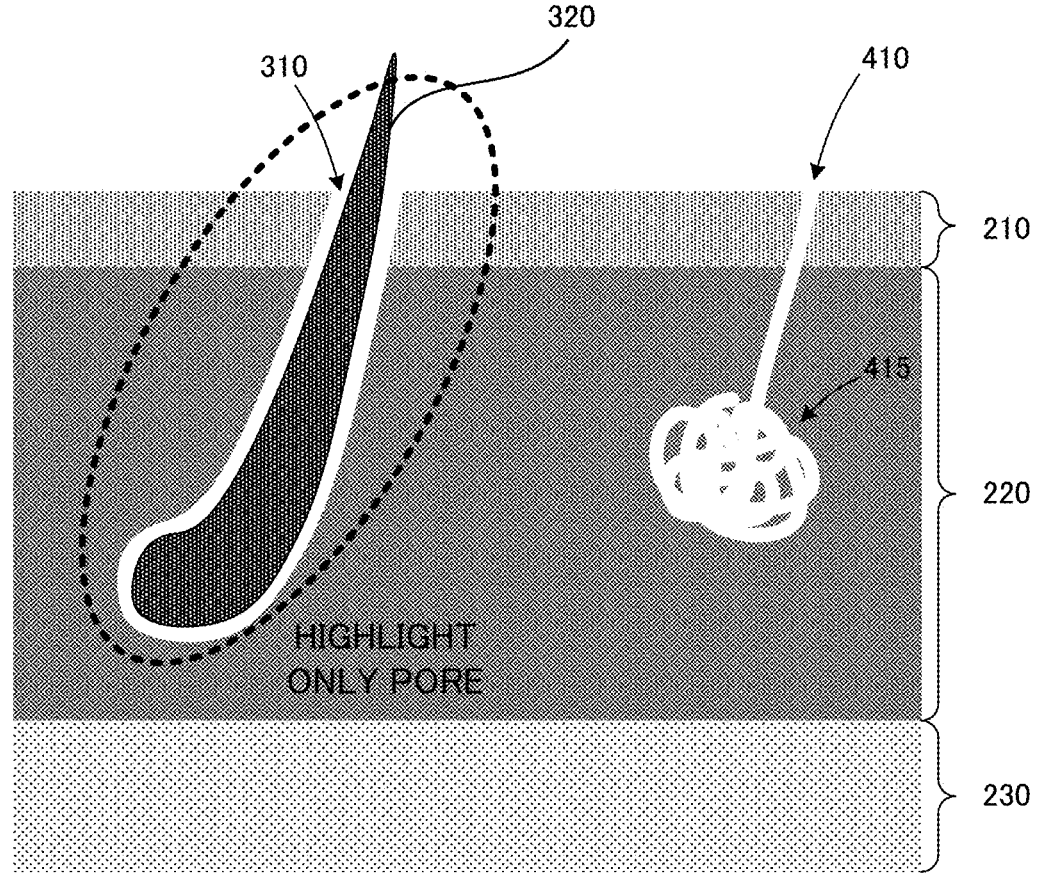
FIG. 20 is a diagram illustrating an example of a tomography image outputted by the bioanalysis system according to the seventh example embodiment.
Figure 21:
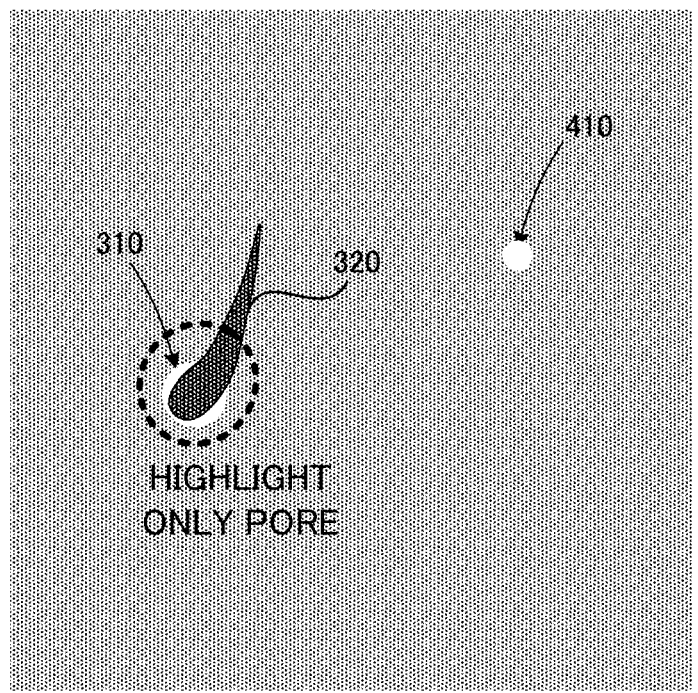
FIG. 21 is version 1 of a diagram illustrating an example of a surface image outputted by the bioanalysis system according to the seventh example embodiment.
Figure 22:
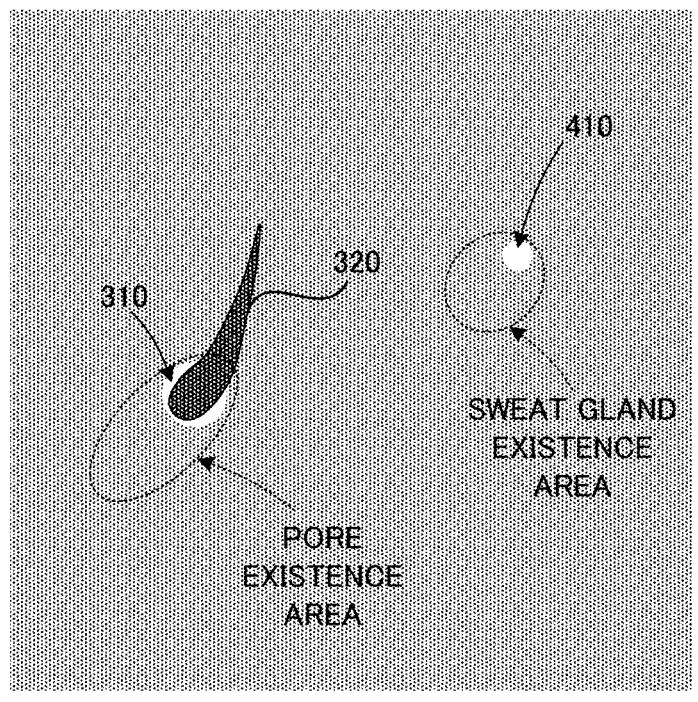
FIG. 22 is version 2 of a diagram illustrating an example of the surface image outputted by the bioanalysis system according to the seventh example embodiment.

Next, with reference to FIG. 20 to FIG. 22, specific output examples by the bioanalysis system 10 according to the seventh example embodiment will be described. FIG. 20 is a diagram illustrating an example of the tomography image outputted by the bioanalysis system according to the seventh example embodiment. FIG. 21 is version 1 of a diagram illustrating an example of the surface image outputted by the bioanalysis system according to the seventh example embodiment. FIG. 22 is version 2 of a diagram illustrating an example of the surface image outputted by the bioanalysis system according to the seventh example embodiment. in FIG. 20 to FIG. 22, for convenience of explanation, one pore 310 and one sweat gland 410 are illustrated, but the tomography image and the surface image including a plurality of pores 310 and sweat glands 410 may be outputted.

As illustrated in FIG. 20, the tomography image outputted from the output unit 150 may display a plurality of pore parts included in the image, in different display aspects, depending on the type of the pore parts. For example, of the plurality of pore parts included in the image, only the pore 310 may be highlighted. That is, the display may be performed in an aspect in which the pore 310 is highlighted, but the sweat gland 410 that is not a pore is not highlighted. The aspect of highlighting may be, for example, changing a color, shading, flashing display, or the like, in addition to displaying to be surrounded by a frame line, as illustrated in the figure. Alternatively, the pore part that is not a highlighting target may not be displayed. That is, the pore 310 that is a highlighting target, may be displayed as it is, while the sweat gland 410 may be deleted from the image. These display aspects may be switchable by the user's operation, for example. Specifically, the highlighting target, the presence or absence of the highlighting, or the like, may be switchable by the user's operation.

As illustrated in FIG. 21, the surface image outputted from the output unit 150 may display a plurality of pore parts included in the image, in different display aspects, depending on the type of the pore parts. For example, of the plurality of pore parts included in the image, only the pore 310 may be highlighted. That is, the display may be performed in an aspect in which the pore 310 is highlighted, but the sweat gland 410 that is not a pore is not highlighted. Alternatively, the pore part that is not a highlighting target may not be displayed. That is, the pore 310 that is a highlighting target, may be displayed as it is, while the sweat gland 410 may be deleted from the image. These display aspects may be switchable by the user's operation, for example. Specifically, the highlighting target, the presence or absence of the highlighting, or the like, may be switchable by the user's operation.

As illustrated in FIG. 22, in the surface image outputted from the output part 150, a pore existence area that is an area in which the pore 310 exists in a deep position of the skin, or a sweat gland existence area that is an area in which the sweat gland 410 exists in a deep position of the skin, may be displayed. The pore existence area and the sweat gland existence area may be areas estimated from the tomography image, for example.

The output unit 150 may display both the tomography image and the surface image, simultaneously. The output unit 150 may switch and display the tomography image and the surface image. In this case, the output unit 150 may display a button for switching, on a display, and may switch and display the tomography image and the surface image by the user's operation. The output unit 150 may enable the user to designate a cross-section in the surface image, and may display the tomography image cut by the cross-section designated by the user.

Technical Effect

Next, a technical effect obtained by the bioanalysis system 10 according to the seventh example embodiment will be described.

As described in FIG. 18 to FIG. 22, according to the bioanalysis system 10 in the seventh example embodiment, at least one of the tomography image and the surface image is outputted on the basis of the position and the type of the pore part. In this way, it is possible to display a plurality of pore parts in the skin of a living body, in an appropriate aspect based on the type of the pore parts.

Eighth Example Embodiment

The bioanalysis system 10 according to an eighth example embodiment will be described with reference to FIG. 23 to FIG. 26. The eighth example embodiment is partially different from the seventh example embodiment only in the configuration and operation, and may be the same as the first to seventh example embodiments in the other parts. For this reason, a part that is different from each of the example embodiments described above will be described in detail below, and a description of other overlapping parts will be omitted as appropriate.

(Functional Configuration)

Figure 23:
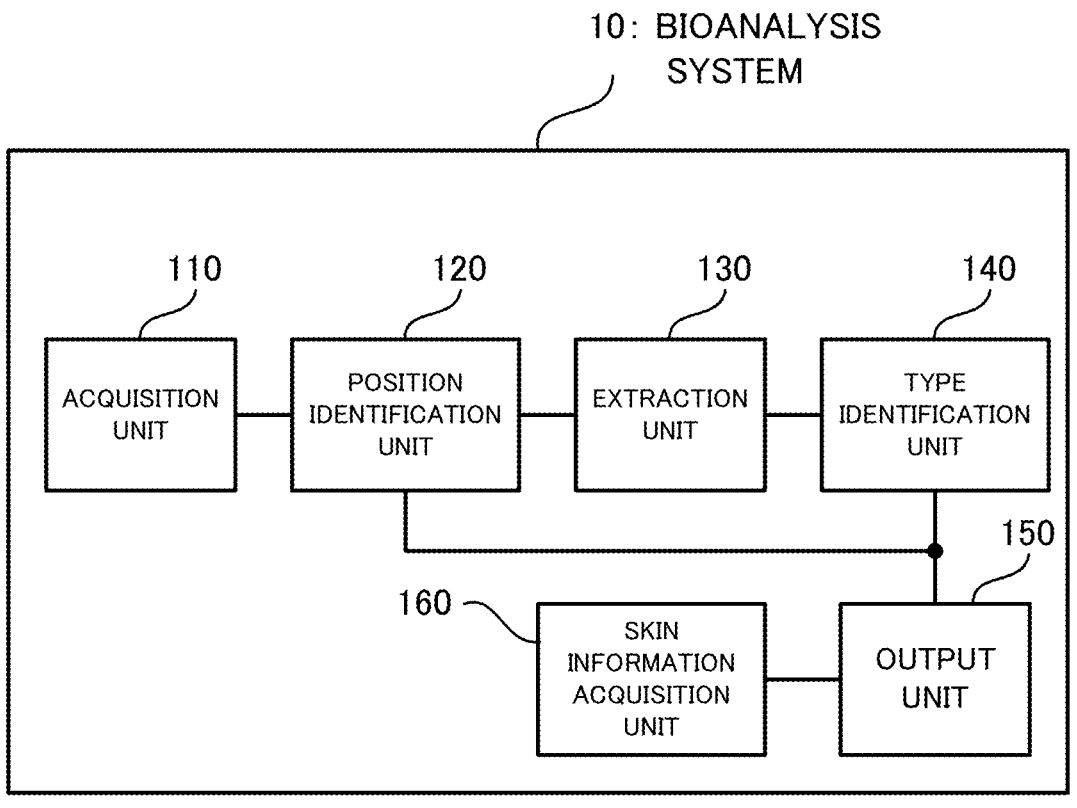
FIG. 23 is a block diagram illustrating a functional configuration of a bioanalysis system according to an eighth example embodiment.

First, with reference to FIG. 23, a functional configuration of the bioanalysis system 10 according to the eighth example embodiment will be described. FIG. 23 is a block diagram illustrating the functional configuration of the bioanalysis system according to the eighth example embodiment. In FIG. 23, the same components as those illustrated in FIG. 18 carry the same reference numerals.

As illustrated in FIG. 23, the bioanalysis system 10 according to the eighth example embodiment includes, as processing blocks for realizing the functions thereof, the acquisition unit 110, the position identification unit 120, the extraction unit 130, the type identification unit 140, the output unit 150, and a skin information acquisition unit 160. That is, the bioanalysis system 10 according to the eighth example embodiment further includes the skin information acquisition unit 160, in addition to the configuration in the seventh example embodiment (see FIG. 18). The skin information acquisition unit 160 may be realized or implemented by the processor 11 (see FIG. 1).

The skin information acquisition unit 160 is configured to obtain additional information about the skin of a living body. The additional information here is information other than information about the position of the pore part identified by the position identification unit 120 and information about the type of the pore part identified by the type identification unit 140. An example of the additional information includes a skin temperature, a skin moisture content, or the like. The skin information acquisition unit 160, however, may obtain information that is not listed here, as the additional information. The additional information obtained by the skin information acquisition unit 160 is configured to be outputted to the output unit 150. The output unit 150 according to the eighth example embodiment is configured to output at least one of the tomography image and the surface image after superimposing the additional information obtained by the skin information acquisition unit 160 on the images.

(Flow of Operation)

Figure 24:
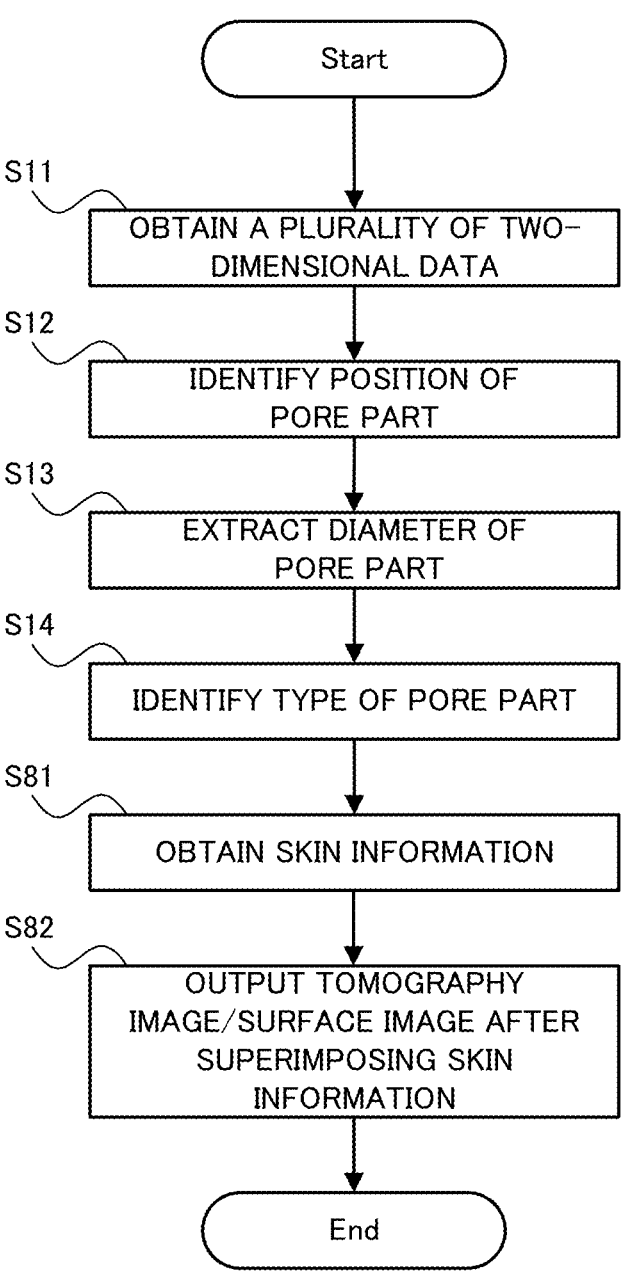
FIG. 24 is a flowchart illustrating a flow of operation of the bioanalysis system according to the eighth example embodiment.

Next, with reference to FIG. 24, a flow of operation of the bioanalysis system 10 according to the eighth example embodiment will be described. FIG. 24 is a flowchart illustrating the flow of the operation of the bioanalysis system according to the eighth example embodiment. In FIG. 24, the same steps as those illustrated in FIG. 19 carry the same reference numerals.

As illustrated in FIG. 24, when the operation of the bioanalysis system 10 according to the eighth example embodiment is started, first, the acquisition unit 110 obtains a plurality of two-dimensional data with different depths in the skin of a living body (step S11). Subsequently, the position identification unit 120 identifies the position of the pore part in the skin of the living body, on the basis of at least one of the two-dimensional data obtained by the acquisition unit 110 (step S12). Subsequently, the extraction unit 130 extracts the diameter of the pore part from each of the plurality of two-dimensional data obtained by the acquisition unit 110 (step S13). Subsequently, the type identification unit 140 identifies the type of the pore part on the basis of the diameter of the pore part extracted by the extraction unit 130 (step S14).

Subsequently, the skin information acquisition unit 160 obtains the additional information about the skin of the living body (step S81). The timing of obtaining the additional information is not particularly limited, and the step S81 may be performed before or after the step S11 to the step S14. Furthermore, the skin information acquisition unit 160 may obtain and store the additional information before the start of a series of processing steps illustrated in the flowchart in FIG. 19, and may read the stored additional information at an appropriate time.

The additional information obtained by the skin information acquisition unit 160 is transmitted to the output unit 150, and the output unit 150 outputs at least one of the tomography image and the superficial image of the skin of the living body after superimposing the additional information on the images (step S82).

Specific Output Examples

Figure 25:
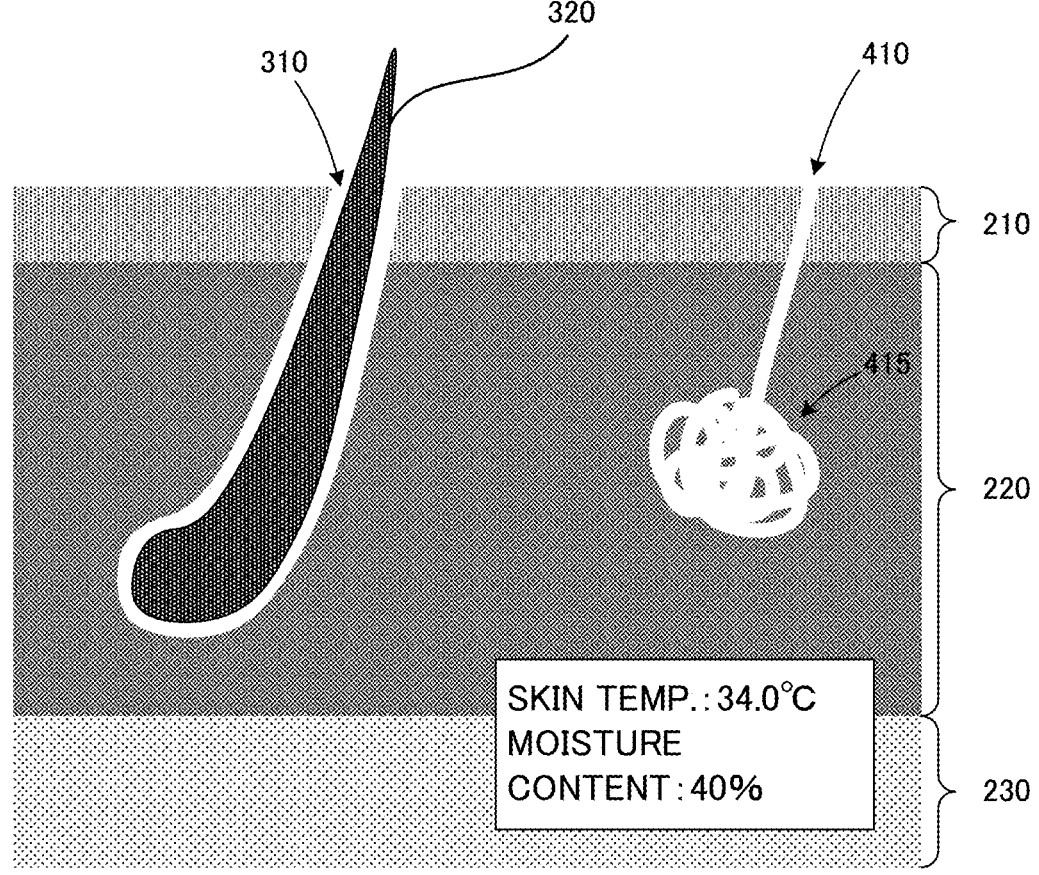
FIG. 25 is a diagram illustrating an example of a tomography image outputted by the bioanalysis system according to the eighth example embodiment.
Figure 26:
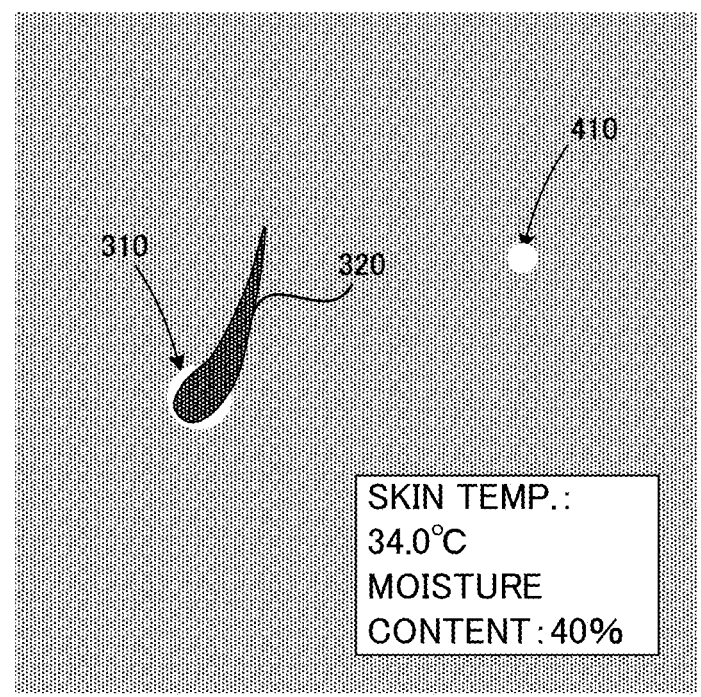
FIG. 26 is a diagram illustrating an example of a surface image outputted by the bioanalysis system according to the eighth example embodiment.

Next, with reference to FIG. 25 and FIG. 26, specific output examples by the bioanalysis system 10 according to the eighth example embodiment will be described. FIG. 25 is a diagram illustrating an example of the tomography image outputted by the bioanalysis system according to the eighth example embodiment. FIG. 26 is a diagram illustrating an example of the surface image outputted by the bioanalysis system according to the eighth example embodiment. In FIG. 25 and FIG. 26, for convenience of explanation, one pore 310 and one sweat gland 410 are illustrated, but the tomography image and the surface image including a plurality of pores 310 and sweat glands 410 may be outputted.

As illustrated in FIG. 25 and FIG. 26, the output unit 150 may output the tomography image and the surface image after superimposing information about the skin on the images. Here, as the information about the skin, a skin temperature is displayed, for example. Alternatively, a moisture content of the skin may be displayed. Furthermore, a plurality of pieces of information may be displayed, such as the skin temperature and the moisture content of the skin. In the example illustrated in the figure, the following is superimposed and displayed as the additional information: namely, the skin temperature is 34.0° C. and the moisture content of the skin is 40%. The display of the additional information may be switchable by the user's operation, for example. Specifically, the display or not-display of the additional information may be switchable by the user's operation. The type and the number of pieces of the additional information displayed may be changeable by the user's operation. The position at which the additional information is displayed may be changeable by the user's operation.

In addition, when the additional information that varies depending on the position of the tomography image and the surface image is superimpose and displayed, the additional information may be superimposed and displayed at a corresponding position on the image. For example, when the skin temperature is different between a right-side area and a left-side area of the image, the skin temperature in the right-side area may be displayed on the right side of the image, and the skin temperature in the left-side area may be displayed on the left side of the image.

Technical Effect

Next, a technical effect obtained by the bioanalysis system 10 according to the eighth example embodiment will be described.

As described in FIG. 23 to FIG. 26, according to the bioanalysis system 10 in the eighth example embodiment, at least one of the tomography image and the surface image with the additional information superimposed is outputted. In this way, it is possible to properly provide the information about the skin of a living body, together with the tomography image and the surface image. The bioanalysis system 10 according to the eighth example embodiment provides a beneficial technical effect in a service of proposing cosmetics suited for the skin, or the like, for example.

Ninth Example Embodiment

The bioanalysis system 10 according to a ninth example embodiment will be described with reference to FIG. 27 to FIG. 32. The ninth example embodiment describes display examples that are applicable to the example embodiments described above, and may be the same as the first to eighth example embodiments in configuration of the system, the flow of the operation, or the like. For this reason, a part that is different from each of the example embodiments described above will be described in detail below, and a description of other overlapping parts will be omitted as appropriate. The following display examples may be displayed on the display or the like of the output apparatus 16 (FIG. 1), for example.

First Display Example

Figure 27:
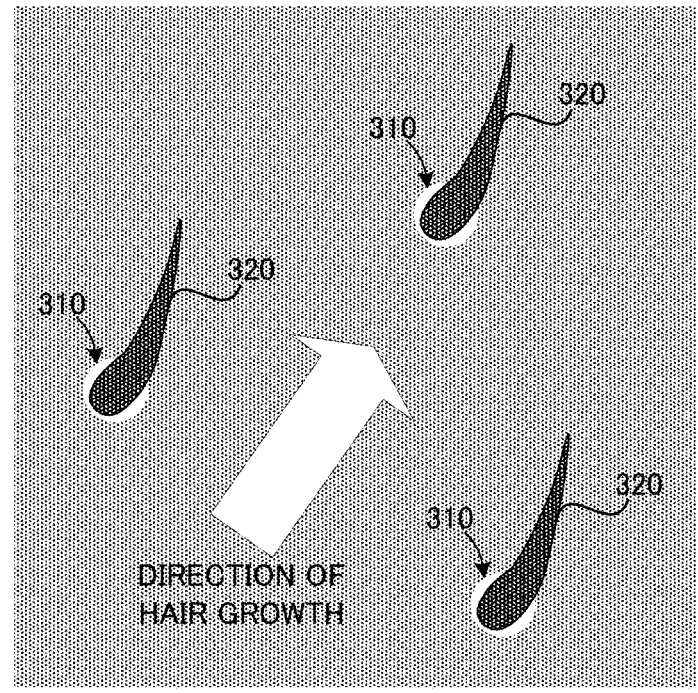
FIG. 27 is a diagram illustrating a first display example by a bioanalysis system according to a ninth example embodiment.

First, with reference to FIG. 27, a first example display of the bioanalysis system 10 according to the ninth example embodiment will be described. FIG. 27 is a diagram illustrating the first display example by the bioanalysis system according to the ninth example embodiment.

As illustrated in FIG. 27, in the first display example, a direction of growth of the hairs 320 (in other words, a direction of hair flow) is displayed by a vector, together with an image of the pores 310 and the hairs 320. In this way, it is possible to inform the user or the like of the direction of growth of the hairs 320, in a visually easy-to-understand manner. The direction of growth of the hairs 320 can be identified from a plurality of two-dimensional data with different depths in the skin of a living body. For example, it can be estimated from a positional relationship between a hair bulb part and a pore surface, or the like.

Second Display Example

Figure 28:
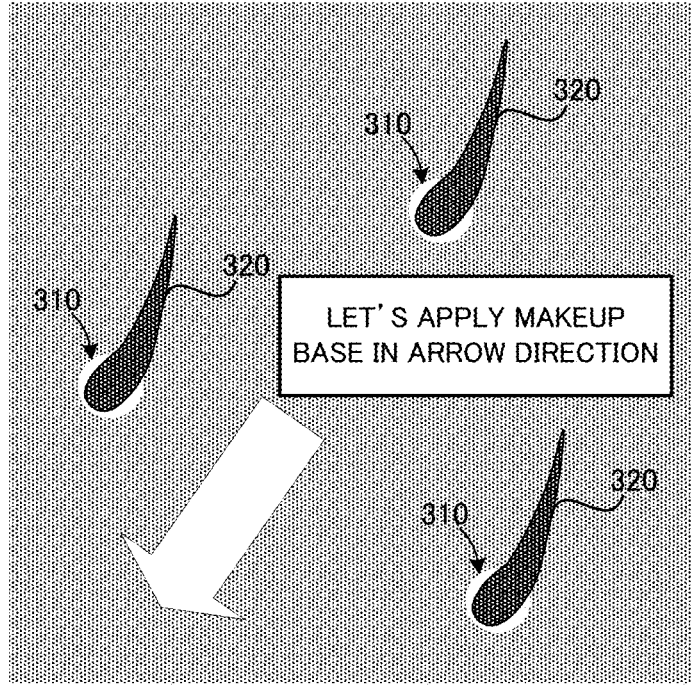
FIG. 28 is version 1 of a diagram illustrating a second display example by the bioanalysis system according to the ninth example embodiment.
Figure 29:
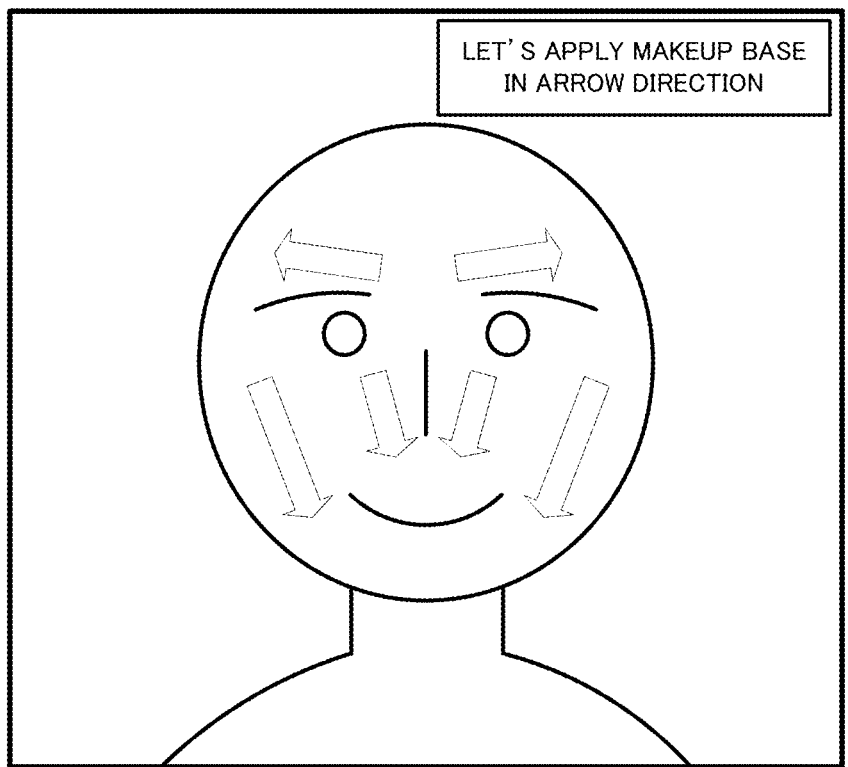
FIG. 29 is version 2 of a diagram illustrating the second display example by the bioanalysis system according to the ninth example embodiment.

Next, with reference to FIG. 28 and FIG. 29, a second exemplary display by the bioanalysis system 10 according to the ninth example embodiment will be described. FIG. 28 is version 1 of a diagram illustrating the second display example by the bioanalysis system according to the ninth example embodiment. FIG. 29 is version 2 of a diagram illustrating the second display example by the bioanalysis system according to the ninth example embodiment.

As illustrated in FIG. 28, in the second display example, a direction of applying cosmetics is displayed by a vector, together with the image of the pores 310 and the hairs 320. For example, when a makeup base is applied, it is known that the pores can be firmly covered by applying it in an opposite direction of a direction of the pores (i.e., the direction of hair growth), and it is possible to prevent the makeup base from sitting or getting clogged in the pores or the like. Therefore, in the second display example, an arrow or the like is displayed to apply the cosmetics in the opposite direction of the direction of hair growth illustrated in the first display example (see FIG. 27).

As illustrated in FIG. 29, in the second display example, the direction of applying the cosmetics may be displayed together with a face image of the user or a facial model. In this case, the direction of applying the cosmetics may be displayed for each face part. In this way, it is possible to inform the user or the like of the direction of applying the cosmetics, in a visually easy-to-understand manner.

Third Display Example

Figure 30:
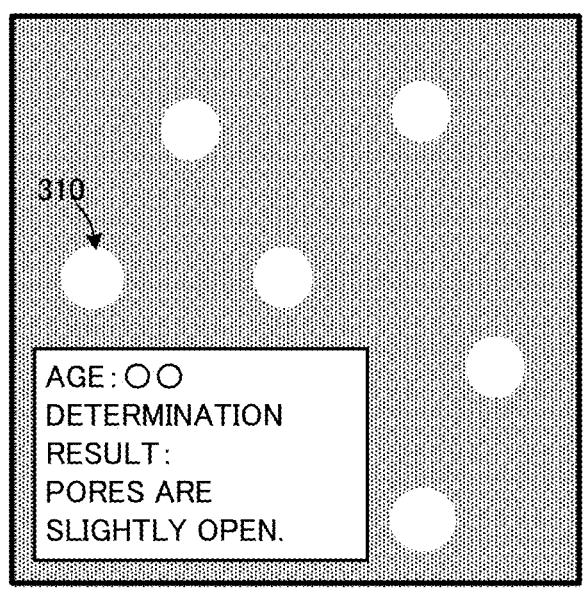
FIG. 30 is a diagram illustrating a third display example by the bioanalysis system according to the ninth example embodiment.

Next, with reference to FIG. 30, a third display example by the bioanalysis system 10 according to the ninth example embodiment will be described. FIG. 30 is a diagram illustrating the third display example by the bioanalysis system according to the ninth example embodiment.

As illustrated in FIG. 30, in the third display, a degree of open pores is displayed together with an image of the pores 310. The degree of open pores may be displayed in accordance with the age of a target person (e.g., the degree of open pores when it is compared with those in the same generation), for example. In this case, the age of the target person may be displayed as illustrated in the figure. The age of the target person may be inputted in advance, or may be estimated from the user's face image, or the like. The degree of open pores may be displayed, such as, for example, "fairly open," "slightly open," "just right," "slightly closed," and "fairly closed." Alternatively, a quantified index (e.g., how many points out of 100) may be displayed for the degree of open pores.

The degree of open pores may be obtained, for example, by keeping a table that stores an average pore size for each age and comparing a detected pore size (e.g., a value detected from the surface image or the tomography image) with the values in the table. The pore size stored in the table may be stored separately for each part of a body. The pore size stored in the table may be stored separately for each air temperature. In this way, if a table is prepared for each part and for each air temperature, it is possible to improve the accuracy of a result of the determination of the degree of open pores. When the degree of open pores is known, it is possible to properly propose the cosmetics that can hide or conceal the pores, for example.

Fourth Display Example

Figure 31:
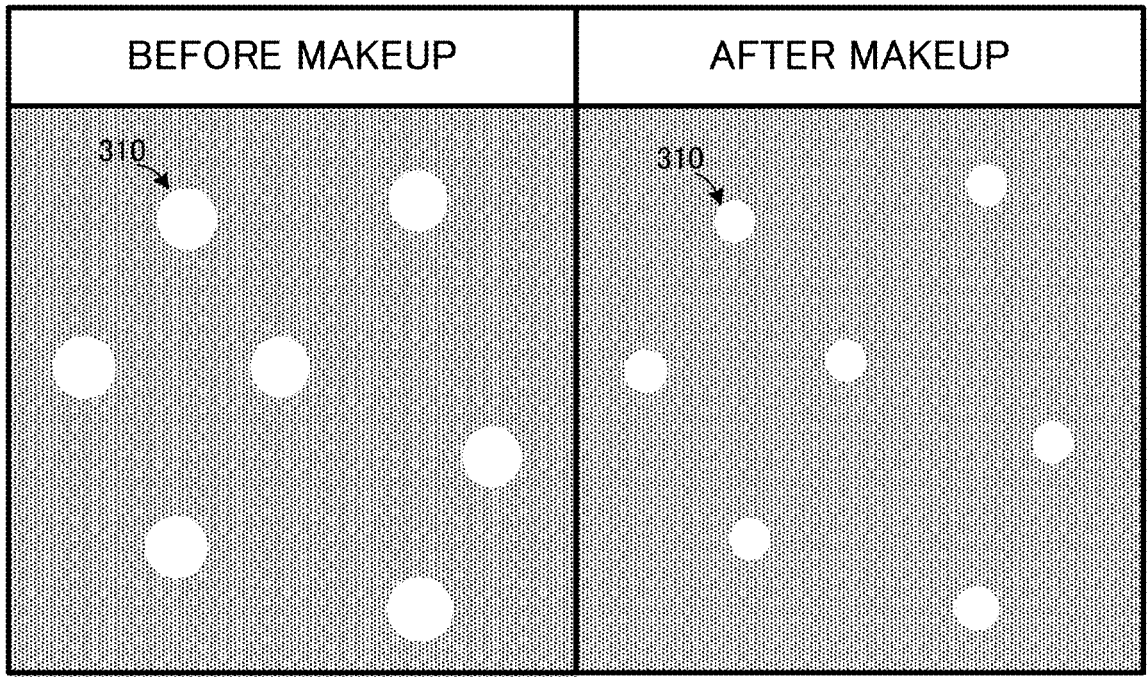
FIG. 31 is version 1 of a diagram illustrating a fourth display example by the bioanalysis system according to the ninth example embodiment.
Figure 32:
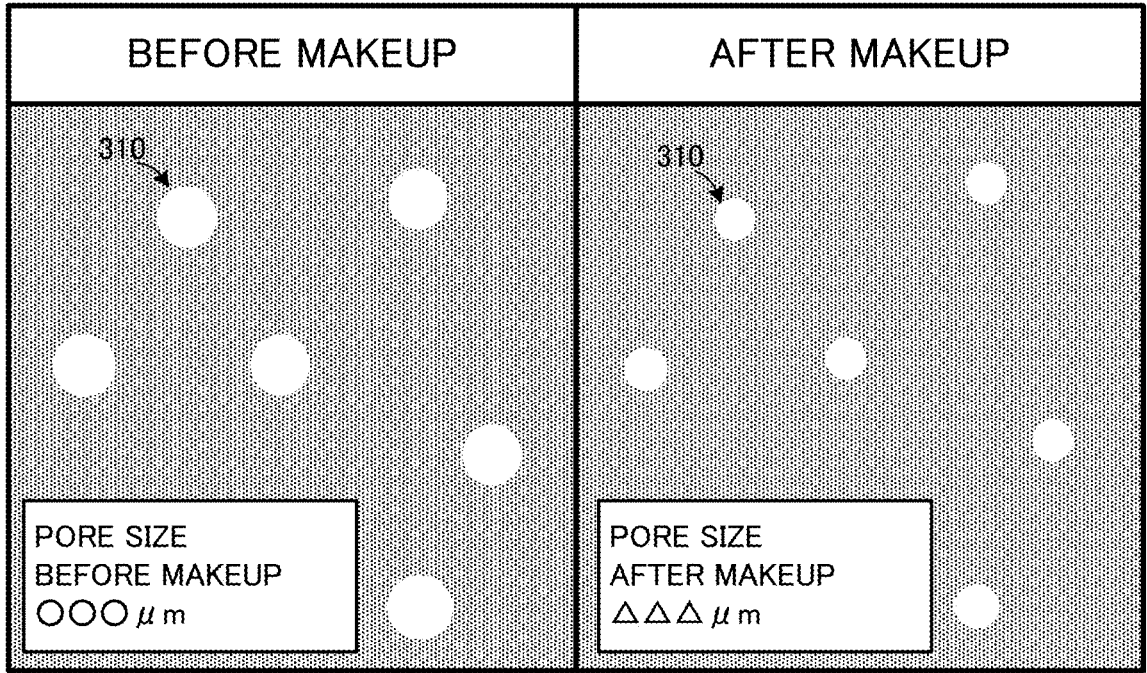
FIG. 32 is version 2 of a diagram illustrating the fourth display example by the bioanalysis system according to the ninth example embodiment.

Next, with reference to FIG. 31 and FIG. 32, a fourth display example by the bioanalysis system 10 according to the ninth example embodiment will be described. FIG. 31 is version 1 of a diagram illustrating the fourth display example by the bioanalysis system according to the ninth example embodiment. FIG. 32 is version 2 of a diagram illustrating the fourth display example by the bioanalysis system according to the ninth example embodiment.

As illustrated in FIG. 31, in the fourth display example, an image of the pores 310 before makeup and an image of the pores 310 after makeup are displayed side by side. In this way, it is possible to inform the target person to what extent the pores are hidden or concealed by the makeup.

As illustrated in FIG. 32, in the fourth display example, the image of the pores 310 before makeup and the image of the pores 310 after makeup may be displayed, together with the size of the pores 310 before makeup and the size after makeup. When the size of the pores 310 is displayed, the size of one pore 320 of the plurality of pores 310 may be displayed, or an average value of the sizes of the plurality of pores 310 may be calculated and displayed. Furthermore, in addition to or in place of the size of the pores 310, a degree to which the makeup makes the pores 310 less visible may be displayed.

<Supplementary Notes>

The example embodiments described above may be further described as, but not limited to, the following Supplementary Notes.

(Supplementary Note 1)

A bioanalysis system according to Supplementary Note 1 is a bioanalysis system including: an acquisition unit that obtains a plurality of two-dimensional data with different depths in a skin of a living body; a position identification unit that identifies a position of a pore part in the skin of the living body from at least one of the plurality of two-dimensional data; an extraction unit that extracts a diameter of the pore part from each of the plurality of two-dimensional data; and a type identification unit that identifies a type of the pore part, on the basis of the diameter of the pore part.

(Supplementary Note 2)

A bioanalysis system according to Supplementary Note 2 is the bioanalysis system according to Supplementary Note 1, wherein the type identification unit is configured to identify that the type of the pore part is a pore.

(Supplementary Note 3)

A bioanalysis system according to Supplementary Note 3 is the bioanalysis system according to Supplementary Note 2, wherein the type identification unit identifies the type of the pore part is a pore when a change rate of the diameter of the pore part in a depth direction is less than or equal to a predetermined first threshold.

(Supplementary Note 4)

A bioanalysis system according to Supplementary Note 4 is the bioanalysis system according to any one of Supplementary Notes 1 to 3, wherein the type identification unit is configured to identify that the type of the pore part is a sweat gland.

(Supplementary Note 5)

A bioanalysis system according to Supplementary Note 5 is the bioanalysis system according to Supplementary Note 4, wherein the type identification unit identifies that the type of the pore part is a sweat gland when a change rate of the diameter of the pore part in a depth direction is greater than or equal to a predetermined second threshold.

(Supplementary Note 6)

A bioanalysis system according to Supplementary Note 6 is the bioanalysis system according to any one of Supplementary Notes 1 to 5, wherein the acquisition unit obtains the plurality of two-dimensional data from three-dimensional tomographic data.

(Supplementary Note 7)

A bioanalysis system according to Supplementary Note 7 is the bioanalysis system according to any one of Supplementary Notes 1 to 6, further including an output unit that outputs at least one of a tomography image and a surface image of the skin of the living body including the pore part, on the basis of the position of the pore part and the type of the pore part.

(Supplementary Note 8)

A bioanalysis system according to Supplementary Note 8 is the bioanalysis system according to claim 7, further including a second acquisition unit that obtains additional information that is information about other than the position of the pore part and the type of the pore part, for the skin of the living body, wherein the output unit outputs at least one of the tomography image and the surface image after superimposing the additional information on the images.

(Supplementary Note 9)

A bioanalysis method according to Supplementary Note 9 is a bioanalysis method including: obtaining a plurality of two-dimensional data with different depths in a skin of a living body; identifying a position of a pore part in the skin of the living body from at least one of the plurality of two-dimensional data; extracting a diameter of the pore part from each of the plurality of two-dimensional data; and identifying a type of the pore part, on the basis of the diameter of the pore part.

(Supplementary Note 10)

A computer program according to Supplementary Note 10 is a computer program that operates a computer to: obtain a plurality of two-dimensional data with different depths in a skin of a living body; identify a position of a pore part in the skin of the living body from at least one of the plurality of two-dimensional data; extract a diameter of the pore part from each of the plurality of two-dimensional data; and identify a type of the pore part, on the basis of the diameter of the pore part.

(Supplementary Note 11)

A recording medium according to Supplementary Note 11 is a recording medium on which the computer program according to Supplementary Note 10 is recorded.

This disclosure is not limited to the examples described above and is allowed to be changed, if desired, without departing from the essence or spirit of this disclosure which can be read from the claims and the entire identification. A bioanalysis system, a bioanalysis method, and a computer program with such changes are also intended to be within the technical scope of this disclosure.

DESCRIPTION OF REFERENCE CODES

10 Bioanalysis system
11 Processor
14 Storage apparatus
16 Output apparatus
110 Acquisition unit
111 Three-dimensional data analysis unit
120 Position identification unit
130 Extraction unit
140 Type identification unit
141 Pore identification unit
142 First threshold storage unit
143 Sweat gland identification unit
144 Second threshold storage unit
150 Output unit
160 Skin Information acquisition unit
210 Epidermis
220 Dermis
230 Subcutaneous fat
310 Pore
320 Hair
410 Sweat gland
415 Coil part

What is claimed is:

1. A bioanalysis system comprising:
at least one memory that is configured to store instructions; and
at least one processor that is configured to execute the instructions to:
obtain a plurality of two-dimensional data with different depths in a skin of a living body;

identify a position of a pore part in the skin of the living body from at least one of the plurality of two-dimensional data;

extract a diameter of the pore part from each of the plurality of two-dimensional data;

identify a type of the pore part, on the basis of the diameter of the pore part; and identify that the type of the pore part is a pore when a rate of change of the diameter of the port part in a depth direction is less than or equal to a predetermined first threshold.

2. The bioanalysis system according to claim 1, wherein the at least one processor is configured to execute the instructions to identify that the type of the pore part is a sweat gland.

3. The bioanalysis system according to claim 2, wherein the at least one processor is configured to execute the instructions to identify that the type of the pore part is a sweat gland when a change rate of the diameter of the pore part in a depth direction is greater than or equal to a predetermined second threshold.

4. The bioanalysis system according to claim 1, wherein the at least one processor is configured to execute the instructions to obtain the plurality of two-dimensional data from three-dimensional tomographic data.

5. The bioanalysis system according to claim 1, wherein the at least one processor is configured to execute the instructions to output at least one of a tomography image and a surface image of the skin of the living body including the pore part, on the basis of the position of the pore part and the type of the pore part.

6. The bioanalysis system according to claim 5, wherein the at least one processor is configured to execute the instructions to:

obtain additional information about the skin of the living body which is different from the position of the pore part and the type of the pore part; and output at least one of the tomography image and the surface image after superimposing the additional information on the images.

7. A bioanalysis method comprising:

obtaining a plurality of two-dimensional data with different depths in a skin of a living body;

identifying a position of a pore part in the skin of the living body from at least one of the plurality of two-dimensional data;

extracting a diameter of the pore part from each of the plurality of two-dimensional data;

identifying a type of the pore part, on the basis of the diameter of the pore part; and identifying that the type of the pore part is a pore when a rate of change of the diameter of the port part in a depth direction is less than or equal to a predetermined first threshold.

8. A non-transitory recording medium on which a computer program that allows a computer to execute a bioanalysis method is recorded, the bioanalysis method including:

obtaining a plurality of two-dimensional data with different depths in a skin of a living body;

identifying a position of a pore part in the skin of the living body from at least one of the plurality of two-dimensional data;

extracting a diameter of the pore part from each of the plurality of two-dimensional data;

identifying a type of the pore part, on the basis of the diameter of the pore part; and identifying that the type of the pore part is a pore when a rate of change of the diameter of the port part in a depth direction is less than or equal to a predetermined first threshold.

* * * * *